US005631158A

United States Patent [19]
Dorai et al.

[11] Patent Number: 5,631,158
[45] Date of Patent: *May 20, 1997

[54] METHODS AND COMPOSITIONS FOR HIGH PROTEIN PRODUCTION FROM NON-NATIVE DNA

[75] Inventors: Haimanti Dorai, Lexington; Herrmann Oppermann, Medway, both of Mass.

[73] Assignee: Creative BioMolecules, Inc., Hopkinton, Mass.

[*] Notice: The portion of the term of this patent subsequent to Oct. 25, 2013, has been disclaimed.

[21] Appl. No.: 461,184

[22] Filed: Jun. 5, 1995

Related U.S. Application Data

[63] Continuation of Ser. No. 143,498, Oct. 25, 1993, abandoned.
[51] Int. Cl.$^6$ .............................. C12N 5/16; C12N 15/09; C12N 15/13; C12N 15/33
[52] U.S. Cl. ....................... 435/172.3; 435/172.2; 435/320.1; 435/70.21; 435/252.3; 530/387.3; 530/867; 536/23.53; 536/24.1; 536/23.72
[58] Field of Search .......................... 435/172.3, 172.2, 435/320.1, 70.21, 240.27, 252.3, 240.1; 530/867, 387.3; 536/23.53, 23.72, 24.1

[56] References Cited

U.S. PATENT DOCUMENTS

| | | |
|---|---|---|
| 4,656,134 | 4/1987 | Ringold . |
| 4,740,761 | 4/1988 | Kaufman . |
| 4,956,288 | 9/1990 | Barsoum . |
| 5,002,874 | 3/1991 | Kaufman . |
| 5,024,939 | 6/1991 | Gorman . |
| 5,091,513 | 2/1992 | Huston et al. . |
| 5,238,820 | 8/1993 | Kaufman . |

FOREIGN PATENT DOCUMENTS

| | | |
|---|---|---|
| 0378382 | 7/1990 | European Pat. Off. . |
| WO87/02707 | 5/1987 | WIPO . |
| WO-A91-05062 | 4/1991 | WIPO . |
| WO86/06409 | 11/1996 | WIPO . |

OTHER PUBLICATIONS

Foecking, et al. (1986) "Powerful and Versatile Enhancer-Promoter Unit For Mammalian Expression Vectors," *Gene* 45:101–105.

Cockett, et al. (1990) "High Level Expression of Tissue Inhibitor Of Metalloproteinases In Chinese Hamster Ovary Cells Using Glutamine Synthetase Gene Amplification," *Biotechnology* 8:662–667.

Cockett, et al. (1991) "The Use of Engineered E1A Genes To Transactivate The hCMV-MIE Promoter In Permanent CHO Cell Lines," *Nucleic Acids Res.* 19:319–325.

McCartney, et al. (1991) "Biosynthetic Antibody Binding Sites: Development of a Single–Chain Fv Model Based On Antidinitrophenol IgA Myeloma MOPC 315," *Journal of Protein Chem.* 10:669–683.

Adams, et al. (1993) "Highly Specific in vivo Tumor Targeting by Monovalent and Divalent Forms of 741F8 Anti-c-erbB-2 Single–Chain Fv," *Cancer Research* 53:4026–4034.

Huston, et al. (1993) "Medical Applications of Single–Chain Antibodies," *Intern. Rev. Immunol.* 10:195–217.

Grinnell et al., "Transactivated Expression of Fully Gamma–Carboxylated Recombinant Human Protein C, An Antithrombotic Factor" *Biotechnology* 5:1189–1192 (1987).

Shepard et al. [J. Clin. Immunol. 11(3) 117–127 (1991)].

West et al. [Virology 10:38–47 (1987)].

Wu et al. [Cell 33:77–83 (1983)] Yodoi et al. [J. Immunol. 131(1):303–310 (1983)].

Maurer [*Animal Cell Culture: a practical approach*, ed. Freshney, chapter 2 pp. 13–31 (1986)].

Yodi et al. JI 131:303–310 (1983).

Rosen et al. (1992), "The BMP Proteins In Bone Formation and Repair," 8 *Trends In Genetics* 3:97–102.

Wong et al. (1985), "Human GM–CSF: Molecular Cloning of Complementary DNA and Purification of the Natural and Recombinant Proteins," 228 *Science* 17:810–815.

Datta et al. (1991), "A Purified Adenovirus 289–Amino–Acid E1A Protein Activates RNA Polymerase III Transcription In Vitro and Alters Transcription Factor TFIIIC," 65 *J. Virology* 10:5297–5304.

Fujita et al. JP 63033386 A2, Chem. Abst.

*Primary Examiner*—Donald E. Adams
*Attorney, Agent, or Firm*—Testa, Hurwitz & Thibeault, LLP

[57] ABSTRACT

Disclosed herein are improved methods and compositions for achieving enhanced protein production expressed from non-native gene constructs, including single chain sFv and derivative sequences. The methods and compositions are particularly useful for creating stably transfected, constitutively expressing immortalized mammalian cell lines that exhibit high recombinant protein productivity while maintaining a low copy number per cell of the non-native recombinant DNA sequence encoding the protein of interest.

26 Claims, 5 Drawing Sheets

METHODS AND COMPOSITIONS FOR HIGH PROTEIN PRODUCTION FROM NON-NATIVE DNA

The United States Government may have certain rights in this application pursuant to SBIR Grant Nos. SSS-4 1 R43 CA39870-01 and SSS-4 2 R44 CA 39870-02 from the National Institute of Health.

This is a continuation of application Ser. No. 08/143,498 filed on Oct. 25, 1993, now abandoned.

FIELD OF THE INVENTION

The application relates generally to the field of recombinant gene expression.

BACKGROUND OF THE INVENTION

Improved methodologies for maximizing recombinant gene expression is an on-going effort in the art. Of particular interest is the development of methodologies that maximize recombinant expression of mammalian genes suitable for producing commercially useful quantities of biologically active proteins. While prokaryotic, typically bacterial, host cell systems have proven capable of generating large quantities of recombinant proteins, these hosts suffer from a number of disadvantages, including an inability to glycosylate proteins, inefficient cleavage of "pre" or "prepro" sequences from proteins (e.g., inefficient post translational modification), and a general inability to secrete proteins. Consequently the art has sought eukaryotic host systems, typically mammalian host cell systems, for mammalian protein production. One feature of such systems is that the protein produced has a structure most like that of the natural protein species, and, purification often is easier since the protein can be secreted into the culture medium in a biologically active form.

A number of problems still exist however, in mammalian culture systems. Specifically, high levels of expression typically are not easily obtained in mammalian systems. In addition, eukaryotic host cells typically have more stringent requirements for culturing and have slower growth rates. Thus, producing large quantities of a recombinant protein requires more than simply culturing a host cell transfected with an expression vector. This is particularly true when the gene of interest is a poorly expressed gene, i.e., is not produced in abundance or is only transiently expressed under natural, physiological conditions. The genes encoding these proteins typically have multiple levels of regulation, often at one or more levels of the expression system, e.g., at the level of transcription, translation, post translation modification, secretion and/or activation. Typically these genes, when stably integrated in unamplified, immortalized cells, produce less than about 10–100 ng protein/$10^6$ cells per ml. Maximizing production of these proteins means identifying means for circumventing these levels of regulation.

Another class of poorly expressed DNA sequences are non-native, biosynthetic or otherwise artificial genes which contain one or more non-native DNA and/or RNA sequences or structures with which the host system is unfamiliar and which may limit and/or otherwise interfere with efficient protein production. Single chain binding proteins, also referred to in the art as "sFv" (single chain Fv) or "BABS" (biosynthetic antibody binding site) molecules are a particular example of such non-native DNA sequences. Typically, these constructs are expressed in *E. coli*, necessitating their purification from inclusion bodies and refolding in vitro. While prokaryotic cell secretion methods can obviate the need for refolding, there are numerous examples of particular sFv proteins that are not secreted from *E. coli* in active form, or do so at unacceptedly low levels. Moreover, it is not uncommon for secreted sFv molecules to form insoluble aggregates in the periplasm.

One approach to achieving enhanced protein production is use of transient cell expression systems wherein cells are transfected with high copy numbers of plasmids that are not expected to integrate in the host cell genome. The plasmids used in transient cell expression systems also can be modified to further enhance their copy numbers during replication post transfection. While the transfection event typically limits the life of these cells to only several generations, reasonable quantities of the desired protein may be produced while the cells remain alive. Because such transient cell systems are short-lived they are not cell systems of choice for commercial production systems. Transient cell systems often are used to screen candidate plasmid or other vector constructions as part of the development of an immortalized, constitutive cell line. But, because transient expression systems are short lived, the long-term productivity of a particular vector construction (or its effect, once integrated, on the viability of a cell after many generations) can not be determined with certainty. Accordingly, a number of plasmid constructions, while productive in transient cell systems, have been determined not to be useful in established cell lines, an event that generally cannot be determined until an established cell line is created.

Two alternative ways primarily focused on by the art for enhancing recombinant gene expression in eukaryotic host systems are enhancing the gene copy number, typically by gene amplification, and enhancing the efficiency of expression of each gene copy. The most common method for enhancing gene copy number is by selecting for gene amplification wherein the host cell is transformed with two genes, linked or unlinked, one of which encodes the desired protein and the other of which encodes an amplifiable selectable marker, such as dihydrofolate reductase (DHFR.) Transformed cells then are cultured in the presence of increasing concentrations of a toxic agent (e.g., methotrexate, when the amplifiable marker is DHFR) whose effects can be nullified by expression of the selectable marker gene. In response to high concentrations of the toxic agent cells survive because they have amplified the copy number of the selectable marker gene and, fortuitously, the desired protein gene. Using this methodology copy numbers in the hundreds and thousands/cell have been achieved.

While gene amplification has proven to be useful, the methodology suffers from several disadvantages pertinent to commercial production. For example, the production of a highly productive cell line by gene amplification alone, e.g., having thousands of copies of the gene of interest, is a time-consuming process often requiring between 6–10 months to complete. Moreover, at very high copy number, verification of the nucleotide sequence integrity for each gene copy in a cell is difficult or not possible. Accordingly, point mutations and other sequence modifications that can alter the biological activity of the protein product may not be detected, and further may pose problems with compliance of government (e.g., FDA) regulations. Moreover, maintenance of such a high copy number requires maintaining the selective pressure by maintaining high levels of the toxic agent in the culture medium. This is both expensive and presents additional regulatory issues when purifying the protein of interest from the culture medium. Finally, and perhaps most importantly, when a gene has multiple levels of expression regulation, merely increasing the copy number of the DNA may not be sufficient to enhance protein production significantly.

One method for enhancing recombinant DNA expression is by means of one or more genes encoding expression effector molecules. Among the effector molecules known in the art are transacting transcription activators which can stimulate transcription of heterologous genes. Examples include the simian virus (SV40) T antigen and adenovirus E1A and E1B proteins which can act on certain viral promoters of heterologous genes, including the cytomegalovirus (CMV) major intermediate early (MIE) promoter. Other molecules reported to have this transactivating activity include the immediate early (IE) proteins of herpes virus, C-myc and genes of the human and simian acquired immunodeficiency virus.

Other viral genes which can effect mammalian protein production are viral translational control effectors, including genes encoding RNA sequences operative to promote translation. Examples include RNA sequences encoded by the adenovirus, such as the VA genes (VA1 and VA2). Such sequences are believed to assist protein production by assisting with translation initiation, probably by association with one or more translation initiation factors. Other examples include RNA sequences that stabilize the transcript.

Cockett et al., ((1990) *Nucleic Acids Research* 19:319–325 and EP application 378,382) describe the use of the adenovirus E1A genes as an alternative to gene amplification for recombinant protein expression in Chinese hamster ovary (CHO) cells, where the gene of interest is under the CMV promoter control. The level of protein produced is asserted to approach levels achievable by gene amplification, thereby obviating the need for gene amplification. Moreover, the authors see no substantial increase in protein productivity when the E1A gene is introduced to an amplified cell line expressing the gene of interest.

U.S. Pat. No. 5,024,939 describes an unamplified transient cell expression system producing "useful" quantities of a desired gene product in 1 to 14 days without having to establish a continuous production cell system. The authors transfect E1A-expressing cells ("293" cells) with a large number of plasmids carrying the gene of interest under CMV promoter control, and demonstrate increased protein production in these cells for the short lives of the cells. Co-transfection of the 293 cells with the adenovirus VA1 gene appears to double the amount of protein produced in these cells.

It is an object of the instant invention to provide a method for enhancing protein production of poorly-expressed non-native DNA sequences by recombinant DNA technology. It is another object of the invention to provide immortalized cell lines suitable for commercial exploitation wherein the cells are stably transfected with the non-native gene of interest and are competent to constitutively express the gene of interest, and to provide methods for producing these cell lines. Still another object of the invention is to provide cell lines, and methods for creating them, exhibiting high non-native recombinant protein productivity while maintaining a low copy number per cell of the recombinant non-native DNA sequences encoding the protein. Yet another object is to provide cell lines that can be adapted to grow in low serum or serum-free medium.

Importantly, it is another object of the instant invention to provide means for producing commercially-feasible quantities of mono- and bifunctional single-chain antibody binding site constructs (sFv) from cultures of immortalized, stably transfected CHO cell lines.

These and other objects and features of the invention will be apparent from the description, drawings, and claims which follow.

SUMMARY OF THE INVENTION

An improvement in recombinant protein production methodologies now has been discovered which has particular application for the expression of "poorly-expressed" non-native DNA sequences. As a result of this invention, commercial scale production quantities of hard-to-produce non-native proteins now can be obtained from stably transfected, constitutively expressing eukaryotic cells. Moreover, the cell lines taught by this invention exhibit high recombinant protein productivity while maintaining a low copy number per cell of the non-native recombinant DNA sequences encoding the protein. The cell lines of the invention also can be adapted to grow in low serum or even serum-free medium without significantly compromising cell growth or protein productivity.

The invention involves the multiple transfection of an immortalized eukaryotic cell with a gene of interest and at least one, and preferably, two expression effector genes of viral origin competent to effect expression of the non-native gene of interest, culturing the transfected cell under appropriate selection conditions such that the transfected DNA is stably integrated into the cell genome, and selecting a clone that expresses at least 1 μg protein/$10^6$ cells/ml at post-logarithmic phase for cells grown in a "batch" or "terminal" culture. In a preferred embodiment, the clone expresses at least 3 μg protein/$10^6$ cells/ml, or at least 6 μg protein/$10^6$ cells/ml. As will be appreciated by those having ordinary skill in the art, higher protein productivity can be obtained by modifying culture conditions to enhance cell growth or increase cell number. In another preferred embodiment, the non-native gene of interest is co-transfected with a means for amplifying the gene, and the cell is cultured under selection conditions that induce gene amplification. While any means for gene amplification is contemplated to be useful, the currently preferred means of gene amplification is by co-transfection of a gene encoding an amplifiable selection marker, such as, for example, DHFR or adenosine deaminase, in operational association with a transcription unit. Most preferably, the amplifiable selection marker gene is on the same nucleic acid or vector that carries the gene of interest.

While the method of the invention is described with reference to a single cell, as will be appreciated by those having ordinary skill in the art, this is only for ease of description, and the method is most efficiently carried out using a plurality of cells.

As used herein, "vector" is understood to mean any nucleic acid comprising a nucleotide sequence of interest, competent to be incorporated into a host cell and recombining with and integrating into the host cell genome. Such vectors include linear nucleic acids, plasmids, cosmids, phagemids and the like.

As used herein, "gene expression" is understood to refer to the production of the protein product encoded by a DNA sequence of interest, including transcription of the DNA and translation of the RNA transcript.

As used herein, "poorly expressed genes" is understood to describe genetic sequences e.g., DNA sequenes that can be acted on by an RNA polymerase to produce an mRNA transcript, which are not easily expressed and for which only low levels, e.g., less than 10–100 ng protein/$10^6$ cells/ml, are produced in an unamplified stably integrated immortalized eukaryotic host cell system, and for which less than about 100–1000 ng protein/$10^6$ cell per ml are produced in a highly amplified cell. As used herein, a highly amplified eukaryotic cell is a transfected cell subcloned sufficiently to contain about 1000 or more copies of the gene of interest stably integrated into the host cell's genome and in operative association with a strong promoter/enhancer unit.

One class of poorly expressed genes for which substantial protein production is difficult to obtain in eukaryotic systems, particularly mammalian cell systems, is the non-native, biosynthetic or otherwise artificial gene, such as genes created by rational design, and which contains one or more non-native DNA and/or RNA sequences or structures with which the host expression system is unfamiliar and which may limit or otherwise interfere with efficient protein production. An example of such an artificial sequence which does not occur in nature is the single chain binding site molecule or single chain Fv ("sFv", also referred to in the art as "BABS," or "biosynthetic antibody binding sites" molecules) wherein a variable light ($V_L$) and variable heavy ($V_H$) chain are encoded in a single DNA sequence, linked by a sequence encoding a polypeptide linker. For a detailed description of these biosynthetic polypeptide chains see for example, Huston et al., 1988, Proc. Nat. Aca. Sci. USA 85: 5879–5883, U.S. Pat. No. 5,091,513 (issued Feb. 25, 1992) and U.S. Pat. No. 5,132,405 (issued Jul. 21, 1992), the disclosures of which are incorporated herein by reference. A representative list of sFv analogue proteins constructed by artisans in the field, along with the composition of linker sequences, the orientation of the $V_H$ and $V_L$ sequences in the gene, and the antigen with which each sFv interacts specifically, is presented in Huston et al. (1993) Intern. Rev. Immunl. 10:195–217, the disclosure of which is incorporated herein by reference. Production of this class of single-chain proteins in mammalian cells generally is low (e.g., less than 1 ng/ml). See, generally S. J. Davis, et al. (1990) J. Biol. Chem. 265:10410–10418 and A. Traunecker, et al. (1991) EMBO J. 10:3655–3659. To date, it is not certain what the limiting step or steps in efficient expression of these genes may be.

Thus, in a preferred embodiment of the invention the poorly expressed DNA sequence encodes a member of the class of proteins called sFv or BABS (biosynthetic antibody binding site protein), as defined in U.S. Pat. No. 5,091,513 (issued Feb. 25, 1992), U.S. Pat. No. 5,132,405 (issued Jul. 21, 1992) and Huston et al. (1993) Intern. Rev. Immunol. 10:195–217, all herein incorporated by reference.

The sFv polypeptide chains provide attractive alternatives to intact immunoglobulins and Fab fragments due to their small size and their stability at concentrations that typically promote dissociation of natural Fv fragments. The molecules have aprticular utility as in vivo targetting agents, whether as immunotargetting agents or as means for targetting effector molecules to an in vivo site of interest. U.S. Pat. Nos. 5,091,513 and 5,132,405; Huston et al., ((1991) Methods in Enzymology 203: 46–88; Huston et al (1993) Int. Rev. Immunol. 10: 195–217) disclose the utility of sFv polypeptides, as well as numerous single chain constructs synthesized from single DNA sequences and which may further comprise ancillary effector proteins, such as a second sFv a cytotoxic agent, or the like.

The sFv molecules mimic native immunoglobulins in their antigen binding structure. Each sFv polypeptide chain comprises an amino acid sequence defining at least two polypeptide domains. These domains are connected by a polypeptide linker spanning the distance between the C-terminus of one domain and the N-terminus of the other.

The amino acid sequence of each domain includes complementarity determining regions (CDRs) interposed between framework regions (FRs) where the CDRs and FRs of each polypeptide chain together define a binding site immunologically reactive with a preselected antigen.

The term "complementarity determining regions" or "CDRs", as used herein, refer to amino acid sequences which together define the binding affinity and specificity of the natural Fv region of a native immunoglobulin binding site, or a synthetic polypeptide which mimics this function. CDRs are not necessarily wholly homologous to hypervariable regions of natural Fv molecules, and also may include specific amino acids or amino acid sequences which flank the hypervariable region and have heretofore been considered framework not directly determinative of complementarity. The term "framework regions" or "FRs", as used herein, refers to amino acid sequences which are found naturally occurring between CDRs in immunoglobulins. These FR sequences may be derived in whole or part from the same immunoglobulin as the CDRs, or in whole or part from a different immunoglobulin. For example, in order to enhance biocompatibility of an sFv to be administered to a human, the FR sequences can be derived from a human immunoglobulin and so the resulting humanized sFv will be less immunogenic than a murine monoclonal antibody.

The amino acid sequence of each variable domain includes three CDRs interspersed between four FRs. The two polypeptide domains that define an sFv molecule contain CDRs interspersed between FRs which together form a binding site immunologically reactive with a preselected antigen. The term "immunologically reactive", as used herein, refers to the noncovalent interactions of the type that occur between an immunoglobulin molecule and an antigen for which the immunoglobulin is specific.

In a preferred aspect of the invention, the CDRs of the polypeptide chain can have an amino acid sequence substantially homologous with at least a portion of the amino acid sequence of CDRs from a variable region of an immunoglobulin molecule from a first species, together with FRs that are substantially homologous with at least a portion of the amino acid sequence of FRs from a variable region of an immunoglobulin molecule from a second species. Preferably, the first species is a non-human species, e.g., mouse, and the second species is human. The CDR sequences in the sFv polypeptide chains are preferably substantially homologous to an immunoglobulin CDR retaining at least 70%, or more preferably 80% or 90%, of the amino acid sequence of the immunoglobulin CDR, and also retaining the immunological binding properties of the immunoglobulin.

Of significance is the invention's achievement of commercially-feasible quantities of single-chain binding sites. Therapeutic uses of such "self-targeted" bioactive proteins offer a number of advantages over conjugates of immunoglobulin fragments or complete antibody molecules: they are stable, less immunogenic and have a lower molecular weight; they can penetrate body tissues more rapidly for purposes of imaging or drug delivery because of their smaller size; and they can facilitate accelerated clearance of targeted isotopes or drugs. The multifunctional proteins described herein offer fewer cleavage sites to circulating proteolytic enzymes, their functional domains are connected by peptide bonds to polypeptide linker or spacer sequences, and thus the proteins have improved stability. Because of their smaller size and efficient design, the multifunctional proteins described herein reach their target tissue more rapidly, and are cleared more quickly from the body. They also have reduced immunogenicity. In addition, their design facilitates coupling to other moieties in drug targeting and imaging application. Such coupling may be conducted chemically after expression of the sFv to a site of attachment for the coupling product engineered into the protein at the DNA level. Active effector proteins having toxic, enzymatic, binding, modulating, cell differentiating, hormonal, or other bioactivity are expressed from a single DNA as a leader and/or trailer sequence, peptide bonded to the sFv. Furthermore, as described in the art, an essentially limitless combination of binding sites and bioactive proteins is possible, each of which can be refined to optimize independent activity at each region of the synthetic protein.

The non-native constructs produced by the invention in high quantities have particular utility as in vivo targeting agents of tumor antigens. The sFv can be conjugated witha radioactive or fluorescent tag, or other means for for detecting localiztion of the sFv to its target antigen in vivo. Alternatively or, in addition, two sFv molecules can be combined, either at the gene level, or post-translationally, to form a multivalent molecule. These molecules may bind the same or different epitopes on a given antigen, or may bind two different antigens. The sFv also can be conjugated with a cancer therapeutic agent, e.g., such as a cytotoxin like ricin, to destroy the cell targetted by the sFv. As will be appreciated by those skilled in the art, this conjugation also can occur at the gene or protein level. In one example described herein,the sFv construct targets antigens characteristic of breast and ovarian malignancies, such as the c-erbB-2 or c-erbB-2 related antigens. A "c-erbB-2-related tumor antigen" is a protein located on the surface of tumor cells, such as breast and ovarian tumor cells and which is antigenically related to the c-erbB-2 antigen. That is, the related antigen can be bound by an immunoglobulin that is capable of binding the c-erbB-2 antigen (e.g. 741F8, 520C9, and 454C11 antibodies. Related antigens also include antigens comprising an amino acid sequence that is at least 80% homologous, preferably 90% homologous, with the amino acid sequence of c-erbB-2 or an amino acid sequence encoded by a DNA that hybridizes under stringent conditions with a nucleic acid sequence encoding c-erbB-2. An example of a c-erbB-2-related antigen is the receptor for the epidermal growth factor.

Other, representative sFvs include the MOPC315 sFv, which binds dinitrophenol and is useful in model studies; the 26-10 sFv, which binds digoxin, and is useful in secretion models and in therapies for reversal of digoxin intoxication, and numerous other constructs described in the art.

As is evidenced from the foregoing, the methods and compositions of the invention provide a large family of reagents comprising proteins, at least a portion of which defines a binding site patterned after the variable region of an immunoglobulin. It will be apparent that the nature of any protein fragments linked to the sFv, and used for reagents embodying the invention, are essentially unlimited, the essence of the invention being the provision, either alone or linked to other proteins, of binding sites having specificities to any antigen desired.

The expression effector molecules useful in the methods and cell lines of the invention preferably are of viral origin and are competent to stimulate transcription and translation. In one embodiment the expression effector molecules of viral origin are encoded in the bovine papilloma virus early region DNA (See Maat, J. et al (1979) *Gene* 6:75 et seq. and *Molecular Cloning: A Laboratory Manual*, 2ed. Sambrook et al. eds., Cold Spring Harbor Laboratory Press, New York (1989), Chapter 16, for a description of this region of the virus.)

In another embodiment, the expression effector molecules of viral origin include trans-acting transcription activators ("transcription transactivators") competent to act on and stimulate the promoter that induces transcription of the gene of interest. Typically, these transactivators are of vital origin and can act on their own or other particular viral promoters. In a preferred embodiment, the transactivating protein is encoded by the adenovirus E1A or E1B gene, the herpesvirus IE gene, C-myc, or the TAT gene of the human immunodeficiency virus (HIV). For example, where the transactivating protein is E1A, the preferred promoters include the constitutive CMV-MIE promoter, and the adenovirus E1A and late region promoters. Where the transactivator is encoded by the TAT gene, a preferred promoter is the HIV-LTR. Other transactivator-promoter combinations are described in the art and are contemplated herein. As described in more detail below, the viral transcription activator gene need not be under the control of a promoter which limits its expression, but such a promoter may be employed.

In another preferred embodiment, the expression effector molecules of viral origin also include RNA sequences operative to promote translation of the transcript encoded by the gene of interest. These sequences may include mRNA stabilizing sequences or sequences which act on the translation machinary itself. For example, currently most preferred sequences are those encoded by the adenovirus, most particularly the adenovirus VA genes, including VA1 and VA2, which currently are believed to act, at least in part by interaction with one or more translation initiation factors. The bovine papilloma virus early region DNA is anticipated to include one or more of these stabilizing sequences.

Preferably, the transfection system comprises both a gene encoding a transcription transactivating sequence and a gene encoding an RNA stabilizing sequence that stimulates translation.

In another preferred embodiment, the transfected cells are subcloned under selective pressure to induce amplification of the gene of interest. The currently preferred method includes the use of a gene encoding an amplifiable selection marker. An example of such a marker gene used with success in the method of the invention includes the DHFR gene, and selection with methotrexate. However, other amplifiable genes are well known in the art and are contemplated herein, including, without limitation, adenosine deaminase and glutamine synthetase. A general description of gene amplification and useful selectable marker genes are described in a number of texts available in the art, including R. E. Kellems, *Gene Amplification in Mammalian Cells* Marcel Dekker, New York (1993). Where the amplifiable selection gene is not dominant acting, the host cell to be transfected preferably is genotypically deficient in the selection gene.

Host cell lines contemplated to be useful in the method of the invention include any eukaryotic cell lines that can be immortalized, i.e., are viable for multiple passages, (e.g., greater than 50 generations), without significant reduction in growth rate or protein production. Where cell lines are to be used to produce a biological intended for administration to humans, the host cell preferably is not a human cell line. Currently preferred cells are those having simple media component requirements, and which can be adapted for suspension culturing. Most preferred are mammalian cell lines that can be adapted to growth in low serum or serum-free medium. Representatvie host cell lines include BHK (baby hamster kidney), NS/0 (mouse myeloma), CHO (Chinese hamster ovary), S2/0 mouse myeloma) and ATT20 (mouse pituitary), and the like. Useful cells can be obtained from the American Type Culture Collection (ATCC), Rockville, Md. or from the European Collection of Animal Cell Cultures, Porton Down, Salisbury SP40JG, U.K.

Where the DNA of interest is a "low expression" or "poorly expressed" gene sequence, the currently most preferred methodology includes co-transfection of the gene of interest, the transactivating gene and the RNA stabilizing sequence, and subcloning candidate cells under amplification conditions so as to produce a cell line that produces at least 1 μg protein/$10^6$ cells/ml, more preferably at least 3μg protein/$10^6$ cells/ml, or at least 6 μg/$10^e$ cells/ml in a "batch" or "terminal" cell culture where the protein is harvested from the culture medium when the cells are in post-logarithmic phase.

An important feature of the invention is that the method of manufacturing a transfected host cell line provides a low copy number of the DNA sequence of interest while still producing high levels of the protein product which may be due, at least in part, to the presence of the viral transcription activator. This feature endows the invention with regulatory utility by easing the burden of compliance with federal good manufacturing practices. For example, low copy number in the transfected cell enabled and disclosed herein will permit ease of documentation and standardization of production methodologies pursuant to U.S. Food and Drug Administration rules and regulations.

With respect to the transfection process used in the practice of the invention, all means for introducing nucleic acids into a cell are contemplated including, without limitation, $CaPO_4$ co-precipitation, electroporation, DEAE-dextran mediated uptake, protoplast fusion, microinjection and lipofusion. A key to the invention is the complement of vectors with which the cell line is transfected, rather than the mechanical or chemical process by which the DNA incorporation is accomplished.

Moreover, the invention contemplates either simultaneous or sequential transfection of the host cell with vectors containing the DNA sequences to be integrated into the genome. In one preferred embodiment, host cells are simultaneously transfected with at least two unlinked vectors, one of which contains the gene of interest (also referred to as the "reporter gene"), and the other of which contains a gene encoding a transcription transactivator. More preferably, genes encoding an amplifiable selection gene, and a translation stimulating sequence also are cotransfected, either by incorporation of these sequences on one or both of the two unlinked vectors, or by simultaneous transfection with a third vector, followed by early transfectant selection based on cell growth and enhanced protein production. Simultaneous transfection permits for random assortment of the genes to be incorporated into the host cell and allows the cells independently to regulate the copy number and expression level of the transfected sequence. Thus, the final optimal combination is determined empirically for each cell, in essence by each cell, bys electing for high protein producing cells that also are healthy, stable transfectants. The exact copy number of the elements an/or the regulation control elements for their expression, may vary among the clones selected, but all are characterized by producing at least 1 μg protein/ml/$10^6$ cells atpost-logarithmic phase in a terminal cell culture.

While there is no reason a priori that all elements can not be transfected on a single vector, as will be appreciated by those skilled in the art, a single vector limits the possible constellations of the elements on the vector and, therefore, in the cell, rather than allowing for their random assortment in vivo. Where all elements, e.g., the gene of interest, the amplifiable marker and the expression effector sequences are transfected on a single vector, the transactivating transcription effector gene preferably is under control of a weakened promoter to limit the expression of this gene sequence.

Alternatively, the DNA sequences can be transfected sequentially. For example, the vector comprising the transcription activator, e.g., E1A, may be transfected first, and its DNA allowed to stably integrate within the host cell genome prior to subsequent transfection with the remaining sequence(s). Also contemplated in the invention is the use of the expression effector genes under weak or strong promoter/enhancer units.

A key to realizing the benefit of the instant invention's enhanced production of poor expressing DNA sequences is culturing the above-described transfected cells in low serum or serum-free medium. The currently preferred serum-free medium is a lipid-modified medium wherein the modification comprises a lipid membrane phosphoglyceride ester degradation product. A representative formulation of the preferred serum-free medium is presented in U.S. Ser. No. 08/124,676 (filed Sep. 22, 1993) and incorporated herein by reference. Other media, including serum-free media are described in the art.

Thus, in view of this disclosure, skilled genetic engineers can construct transfectants which overcome the production problems associated with certain non-native low expression genes. Specifically, those skilled in recombinant DNA techniques can design appropriate DNA vectors encoding for the non-native protein of interest, an amplifiable marker gene, transcription activators, and translation stimulators, and then use the methods of manufacturing transfectants disclosed herein to obtain large quantities of proteins. Such proteins can be non-native forms or truncated analogs, as well as muteins, fusion proteins, or other constructs capable of mimicking the binding activity of the antibody protein of interest in vivo.

BRIEF DESCRIPTION OF THE DRAWINGS

The foregoing and other objects and features of the invention, as well as the invention itself, may be more fully understood from the following description, when read together with the accompanying drawings, in which:

FIG. 1A depicts a time line corresponding to the protocol depicted in FIG. 1B. FIG. 1B further depicts the individual steps of the selection protocol, including transfection (I), cloning (II and III), amplification (IV), cell culture (V and VI), and non-native protein purification (VII).

FIG. 2 depicts restriction maps of three exemplary vectors for transfecting cells with the adenovirus E1A or VA1 genes.

DETAILED DESCRIPTION

A methodology and cell line useful for the large scale production of recombinant mammalian gene expression now has been discovered. The method has particular utility in providing useful quantities of protein encoded by non-native "hard-to-express" genes. The method of the invention can produce stable, immortalized mammalian cell lines that constitutively express a DNA sequence of interest to produce protein at a concentration of at least 1 μg protein/$10^6$ cells/ml without relying on high copy numbers of the gene of interest. Moreover, the method of the invention requires substantially shorter times for producing high expressing, fully amplified cells. Also as described herein, using the vector constructs and cotransfection protocols disclosed herein, reasonable protein production in a variety of mammalian transient expression systems also can be obtained.

Figure 1:
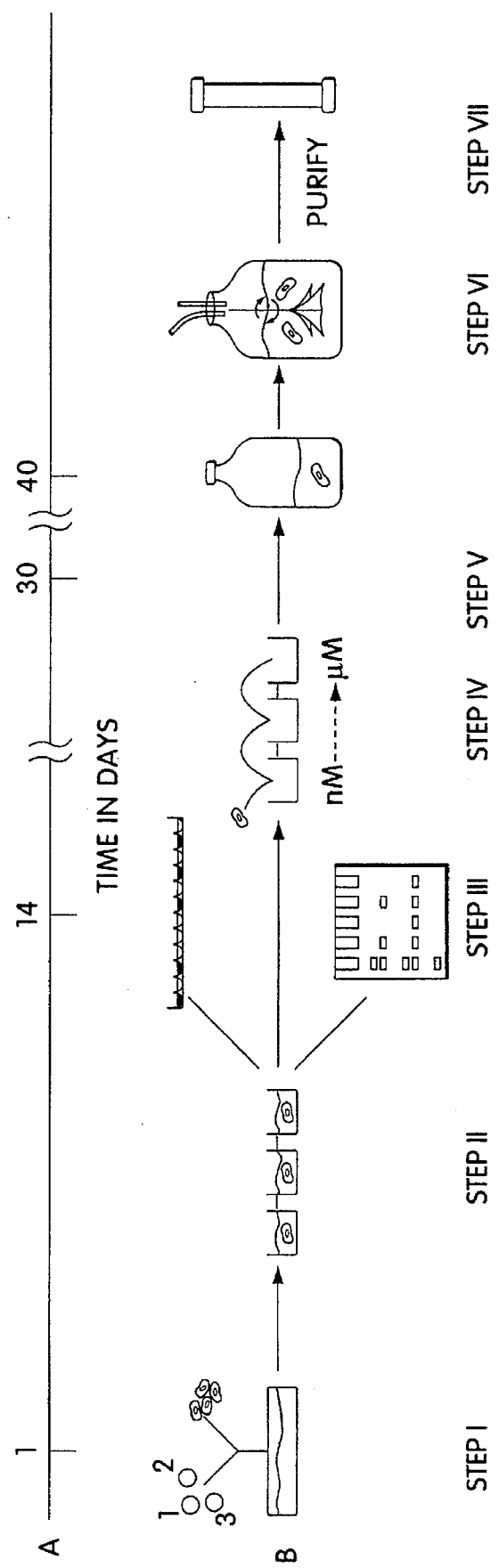
FIG. 1 is a schematic representation of a selection protocol of the invention.

A general selection protocol useful in the method of the invention is depicted in FIG. 1. As can be seen in step I of the protocol, an immortalized eukaryotic host cell, typically a mammalian cell, is transfected with nucleic acids carrying three DNA sequences. The first DNA sequence carries the reporter gene (gene of interest) operatively associated with a transcription promoter/enhancer unit of viral origin. The second DNA carries a viral gene encoding a transactivating protein competent to act on and stimulate transcription from the viral promoter unit that induces transcription of the reporter gene. The third DNA carries a viral gene encoding an RNA stabilizing sequence operative to promote translation of the reporter gene transcript. In FIG. 1, these DNA sequences are carried on separate vectors and the vectors are transfected simultaneously. However, as will be appreciated by those having ordinary skill in the art, the DNA sequences can be transfected sequentially. For example, the cell first can be transfected with one or more nucleic acids carrying the translation promoter sequence and/or the transcription transactivator sequences, and stable integrants obtained, and the cell subsequently transfected with the reporter gene. In addition, two or three of the desired DNA elements (e.g., transcription transactivator, translation effector, reporter gene) can be carried on a single nucleic acid. Where two of te three sequences are carried on a single vector, combinations that may be particularly useful include the viral effector sequences, or the reporter gene and the translation effector sequence. Where all three sequences are carried on a single vector, means for modulating expression of the transcription transactivator may need to be provided. For example, the adenovirus E1A gene generally is believed to interfere with cell growth at high levels of expression. Where the E1A gene is transfected on a separate nucleic acid than that of the reporter genes, for example, the sequences can assort randomly, in a given cell, increasing the possibility of selecting for a clone that expresses optimal levels of both genes. Because the range of assortment events will be reduced where the genes occur on a single nucleic acid, means for modulating, e.g., limiting the E1A gene expression, for example, by means of a weakened promoter, may be required.

In step II of FIG. 1, transfected cells are replated, e.g., in individual wells and in selective medium, grown to confluency, and the concentration of reporter protein produced (the protein of interest) determined from aliquots of culture medium taken from each well, typically by ELISA or Western blot (step III.) Candidate cells then are cloned/amplified by multiple passages in a limited dilution series in the presence of increasing concentrations of amplification medium, until high expressing, fully amplified cells are obtained, (step IV of FIG. 1.) Without being limited to a particular theory, transfection with the viral transcription transactivating gene appears to limit the degree of amplification allowed in a cell so maximum amplification clones can be achieved at a faster rate and, in the presence of lower concentrations of toxic agent than in cells amplified in the absence of the viral effector genes. Moreover, the presence of the transcription and translation effector genes work synergistically to increase expression from each gene copy. In the method of the invention, step IV occurs in fewer steps than in cells amplified in the absence of the viral effector genes, (typically requiring only about one month vs six months.) Once clones exhibiting the desired protein production level are obtained (step V), cloned cells can be cultured in a large-scale production protocol (e.g., at least 2 liters) (step VI) to produce large quantities of the desired protein, which then can be purified from the culture medium using a standard, desired methodology (step VII).

Following the method outlined herein, stable, high producing clones can be obtained. The combination of viral effector genes has a synergistic effect on protein production, enhancing levels beyond those achievable in the presence of only one of the two effector genes or by gene amplification alone for poorly expressed genes. Moreover, where the reporter gene is a poorly expressed gene capable of producing protein at less than 100-1000 ng/$10^6$ cells/ml in a highly amplified cell, the method and cells of the invention which combine the step of cotransfection with viral effectors and the step of amplification of the reporter gene, unexpectedly can increase the level of protein produced beyond the level obtained using either step alone.

Provided below are detailed descriptions of the various elements that comprise the methods and compositions of the invention, as well as methods for their application, and numerous, nonlimiting examples which 1) illustrate useful, exemplary vector constructions, transfection protocols, useful cell sources, and culturing, selection and subcloning protocols; 2) provide assays for testing candidate cells for their protein productivity and cell growth capabilities; and 3) provide methods for culturing cells in low serum or serum-free media. Also provided are examples demonstrating the method of the invention with a variety of sFv constructs in two different mammalian cell systems: in 293 cells, which are an E1A-expressing cell line useful in transient cell systems, and in Sp2/0 myeloma cells, demonstrating that reasonable quantities of sFv molecules now can be produced from mammalian cells, in both transient and immortalized cell systems wherein the DNA is stably integrated into the host genome.

I. Useful Cells

Any immortalized eukaryotic cell line suitable for long term culturing conditions is contemplated to be useful in the method and compositions of the invention. Useful cell line should be easy to transfect, are capable of stably maintaining foreign DNA with an unrearranged sequence, and have the necessary cellular components for efficient transcription, translation, post-translation modification, and secretion of the protein. Where the cell line is to be transfected with a non-dominating selection gene, the cell line genotype preferably is deficient for the endogenous selection gene. Preferably, the cell line also has simple media composition requirements, rapid generation times, and can be adapted to grow in a suspension culture. Particularly useful cell lines are mammalian cells, including myeloma, HeLa, fibroblast, embryonic and various tissue cells, e.g., kidney, liver, lung and the like. A large number of cells now are available through the American Type Culture Collection (ATCC, Rockville, Md) or through the European Collection of Animal Cell Cultures (ECACC) (Porton Down, Salsbury, SP4 0JG, U.K.).

II. Useful Promoter Units for Reporter Genes

The reporter gene should be operatively associated with a promoter unit capable of being stimulated by a viral transacting transcription activator as described herein. Useful promoters include the human cytomegalovirus major intermediate-early promoter (hCMV-MIE) or the adenovirus early promoter (E1A, E1B promoter), or the adenovirus late region promoter. Preferably, the CMV-MIE promoter is a intron-free form of the promoter, so-called the CMV-MIE "short" promoter. CMV promoter sequences or plasmids containing them can be purchased commercially, e.g. from Invitrogen, Inc., Palo Alto (pCDM8) and from Clontech, Inc., Palo Alto. Preferably, the transcription further is stimulated by the inclusion of a cis-acting enhancer sequence, e.g., the mouse mammary tumor virus long terminal repeat (MMTV-LTR) or the Rous sarcoma virus long terminal repeat (RSV-LTR.) Enhancer sequences or plasmids containing them also are commercially available (e.g., from Invitrogen Inc., San Diego, or Clontech Inc., Palo Alto.) and/or also are available through the ATCC and ECACC.

III. Useful viral expression effector genes

The viral expression effector genes useful in the methods and cell lines of the invention are competent to act on the promoter that induces transcription of the reporter gene and/or to act on the reporter gene's transcript or the translation machinery.

At least one of the expression effector genes is a viral transacting transcription activator. Useful sequences include those encoded by the adenovirus -2E1A and E1B genes, as well as by the bovine papilloma virus early region DNA. Details on these sequences and vectors carrying these sequences can be found in Maat, J. et al. (1979) *Gene* 6:75, and in EP 0378,382 and Cockett, (1990) *Nucleic Acids Research* 19:319–325 all incorporated herein by reference. Whole bovine papilloma virus DNA can be obtained commercially, e.g., from IBI., New Haven (Catalog #3320.)

The authors of EP 0378,382 state that appropriate levels of the transcription activator can be obtained by choice of a suitable promoter/enhancer unit for its transcription (e.g., a weak promoter is preferred and a stable transcription activator expressing cell is produced before transfection with the reporter gene.) Alternatively, and as currently preferred herein, the activator gene is simultaneously co-transfected together with the reporter gene, and the transfected cells individually allowed to determine the appropriate, combined level of all recombinant, expressed genes, including the optimal level of the activator gene product for that cell when present in the cell in combination with the reporter gene and gene product.

The second viral effector preferably is a translation activator, preferably an RNA sequence competent to enhance translation of the reporter gene. Preferably, the RNA sequence is encoded by an adenovirus VA gene, preferably at least VA1. Other useful sequences include a portion of the bovine papilloma virus early region DNA. Details of these sequences also can be found in Maat, J., et al. (1979) *Gene* 6:75, EPO 3378, 382 and Cockett et al. (1990) *Nucleic Acids Research* 19: 219–325; in Schneider et al. (1984) *Cell* 37:291 et. seq.; and in Thimmappaya et al. (1982) *Cell* 31: 543–551, the disclosures of which all are incorporated herein by reference. Like the transcription activator sequence, the translation activator sequence may be transfected under control of its own promoter/enhancer unit, or under a stronger or weaker promoter unit. The choice of promoter/enhancer unit is less critical, as high expression clones having the optimal combination of activator and reporter gene sequences will be determined empirically by the screening and selection protocol in the preferred embodiment of the invention.

By screening for good cell growth and selecting for high reporter gene expression, optimal concentrations of all elements for maximal expression of a given reporter gene more easily is obtained than by artificially predetermining the level any one element should have in the cell.

IV. Vector Construction Considerations

Optimal vector design for transfection into eukaryotic cells should include appropriate sequences to promote expression of the gene of interest as described supra, including appropriate transcription initiation, termination, and enhancer sequences, as well as sequences that enhance translation efficiency, such as the Kozak consensus sequence. Preferred DNA vectors also include a marker gene as a means for selecting for the presence of the vector DNA in a cell. The marker gene also may provide means for amplifying the copy number of the gene of interest, and may also include a second gene for resistance to cytotoxins.

Substantial progress in the development of mammalian cell expression systems has been made in the last decade, and many aspects of these systems' features are well characterized. A detailed review of the state of the art of the production of foreign proteins in mammalian cells, including useful cell lines, protein expression-promoting sequences, marker genes, and gene amplification methods, is disclosed in Bendig, Mary M., (1988) *Genetic Engineering* 7: 91–127.

V. Transfection Considerations

Any method for incorporating nucleic acids into cells of interest is contemplated in the method of the invention. Calcium phosphate ($CaPO_4$), followed by glycerol shock is a standard means used in the art for introducing vectors, particularly plasmid DNA into mammalian cells. A representative method is disclosed in Cockett et al. (1990) *Biotechnology* 8: 662–667, incorporated herein by reference. Other methods that may be used include electroporation, protoplast fusion, particularly useful in myeloma transfections, microinjections, lipofections and DEAE-dextran mediated uptake. Methods for these procedures are described in F. M. Ausubel, ed., *Current Protocols in Molecular* John Wiley & Sons, New York (1989).

Generally, plasmids are transfected in equal molar concentrations and cells are plated at a density of about 1–2 $10^6$ cells/dish. As will be appreciated by those having skill in the art, optimal DNA concentrations per transfection will vary by transfection protocol. For a calcium phosphate transfection, for example, preferably 5–10 μg plasmid DNA per plasmid type is transfected. So, where a simultaneous triple transfection is contemplated, 15–30 μg are transfected in total. In addition, the DNA to be transfected preferably essentially free of contaminants that may interfere with DNA incorporation. A standard means used in the art for purifying DNA is by ethydium bromide banding.

VI. Amplification Considerations

One of the better characterized methods of gene amplification in mammalian cell systems is the use of the selectable DHFR gene in a dhfr- cell line. Generally, the DHFR gene is provided on the vector carrying the gene of interest, and addition of increasing concentrations of the cytotoxic drug methotrexate leads to amplification of the DHFR gene copy number, as well as that of the associated gene of interest. DHFR as a selectable, amplifiable marker gene in transfected Chinese hamster ovary cell lines (CHO cells) is particularly well characterized in the art. The instant invention may be practiced using this particular amplification marker. Other useful amplifiable marker genes include the adenosine deaminase (ADA) and glutamine synthetase (GS) genes. (See, R. E. Kellems, *Gene Amplification in Mammalian Cells*, Marcel Dekker, New York (1993).)

VII. Exemplary Large Scale Culture Production Protocols

Any means available or known in the art for large scale eukaryotic cell culturing (e.g., at least 2 L) is anticipated to be useful for culturing the cells taught by this invention. Two general culturing methodologies practiced in the art are the "continuous flow" systems, where cells are exposed to fresh media at regular intervals to replenish any spend nutrients, and the "terminal" or batch culture system, where cells are grown to confluency under a defined set of culture parameters, and the production medium harvested when cells have entered post-logarithmic phase. In addition, cells may be grown as a suspension culture or as attached, monolayers of cells.

The type of culture system used and the media replenishment regimen chosen are determined by the host cell. For example, some mammalian cell lines are not adaptable to suspension cultures while others are unable to remain securely attached to a substrate. Additionally, some cell lines are highly vulnerable to the shear forces associated with suspension and/or bioreactor culture conditions. In the case of these cell lines, addition of agents such as anti-foam and/or shear-minimizing agents may permit use of suspension cultures. Another factor critical in the choice of culture system is the host cell's gas requirements, with gas transfer and gas composition being two important considerations for optimal cell growth in vitro. Numerous references are available that describe means for creating large scale culture conditions and general considerations. Exemplary references include R. J. Freshney, *Animal Cell Culture: A Practical Approach* 2d.ed., Oxford University Press, New York, 1992, and M. Butler, *Mammalian Cell Biotechnology: A Practical Approach*, Oxford University Press, New York, 1991.

VIII. Media Considerations

Transfectants obtained with the above-described preferred protocol are initially conditioned in media containing serum proteins. Preferably, under production conditions, the cells are adapted to growth in low serum or serum-free conditions, to limit interference with protein purification. Useful media includes media containing 0.1%–0.5% dialyzed fetal calf serum. In a preferred embodiment, the low serum or serum-free media is supplemented with one or more lipid membrane phosphoglyceride ester degradation products, as disclosed in U.S. Ser. No. 08/124,676, filed Sep. 22, 1993 and incorporated herein by reference. Other media components useful in production protocols include protease inhibitors. A representative reference detailing growth supporting media considerations for mammalian cell culture includes *ATCC Media Handbook*, Cote et al., ed., American Type Culture Collection, Rockville, Md. (1984).

As indicated above and as will be appreciated by these having ordinary skill in the art, particular details of the conventional means for transfection, expression, and purification of recombinant proteins are well documented in the art and are understood by those having ordinary skill in the art. The instant invention enables and discloses improvements to these conventional means comprising a combination of transfection vectors which achieves markedly enhanced recombinant expression of low expressing genes including genes encoding morphogenic proteins, using immortalized, eukaryotic cells.

Further details on the various technical aspects of each of the steps used in recombinant production of foreign genes in mammalian cell expression systems can be found in a number of texts and laboratory manuals in the art, such as, for example, F. M. Ausubel et al., ed., *Current Protocols in Molecular Biology*, John Wiley & Sons, New York, (1989.)

EXAMPLE 1

I. Construction of Representative Expression Effector Vectors

Figure 2A:
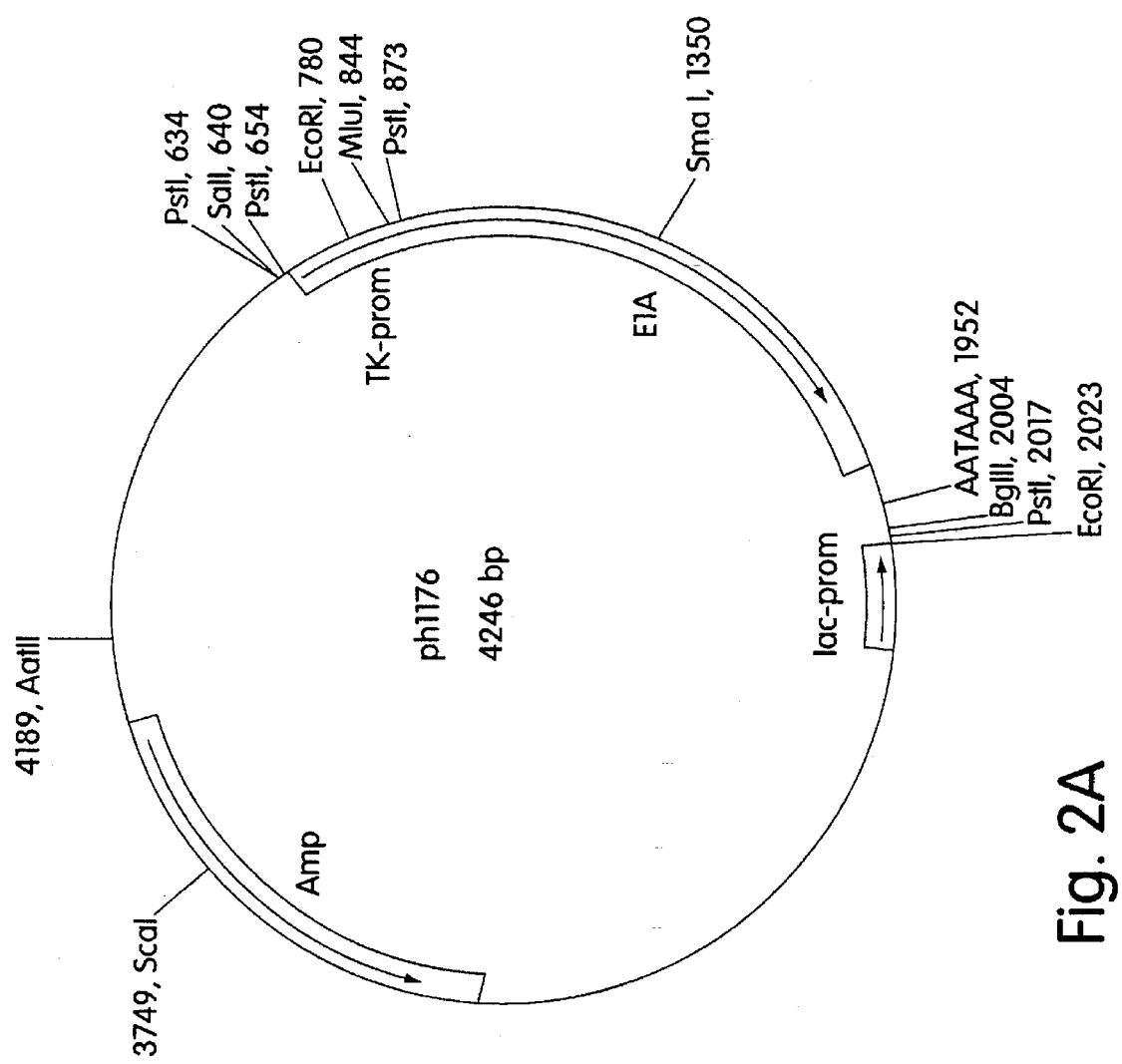
FIG. 2A depicts the pH 1176 vector employing the E1A gene.

The pH1176 vector (FIG. 2A) employs the adenovirus E1A gene (Seq. ID No. 1) as a transactivating transcription activator under the control of the thymidine kinase (TK) promoter. The E1A coding region was isolated by polymerase chain reaction (PCR) with adenovirus-2 DNA as template and priming the reaction with synthetic oligo nucleotide primers that hybridize to gene terminal sequences (upper and lower strand, Seq. ID Nos. 2 and 3) with a commercially available thermal cycler and reagent kit (e.g., GeneAmp, Perkins-Elmer Corp., Norwalk) and following manufacturer's instructions in a standard protocol, (see, for example, Saiki et al. (1985) *Science* 230:1350–1354.) The fragment was cloned in a standard, commercially available pUC cloning vector (e.g., SK-Bluescript, Stratagene, Inc., Palo Alto.) The herpes simplex virus thymidine kinase promoter was isolated as a 5' SalI to 3' HindII fragment from another plasmid (pTK-HGH, Allegro Systems, San Juan Capistrano) and fused to a StuI site upstream of the E1A coding region. The fragment bearing the TK-promoter and E1A was cloned in a pUC plasmid resulting in plasmid pH1176 (FIG. 2A). Seq. ID No. 1 describes the nucleotide sequence of the Pst 1-ERI fragment of pH1176 and includes the E1A gene under TK control. Maintenance of low copy number in the transfected cells under selective pressure can be monitored to ensure incorporation and maintenance of the E1A gene, e.g., by Southern blot and/or by gel assay, wherein the level of detected target DNA is compared to a known quantity.

Figure 2B:
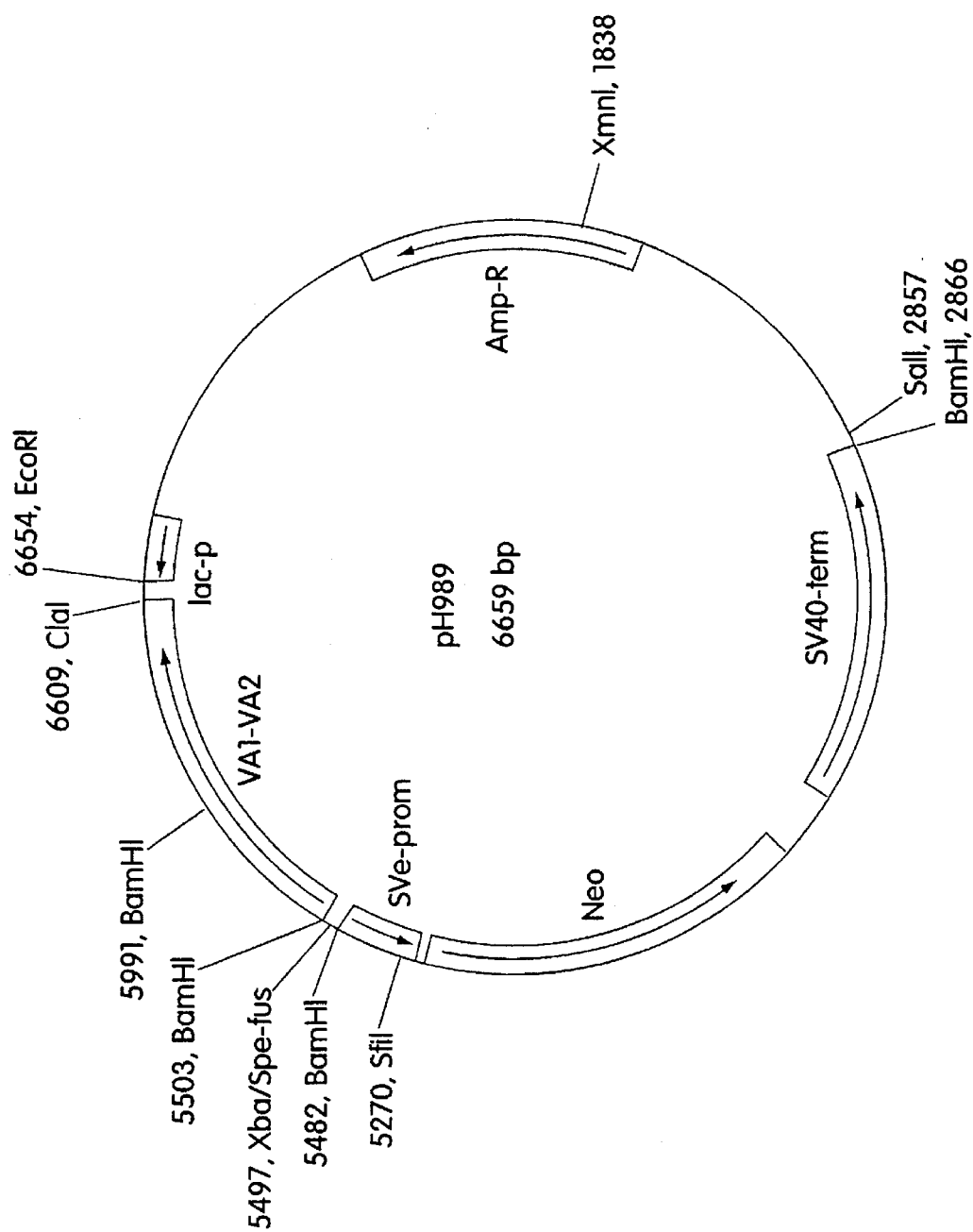
FIG. 2B depicts the pH 989 vector and FIG. 2C depicts the pH 1130 vector, both vectors employing the VA1 gene.
Figure 2C:
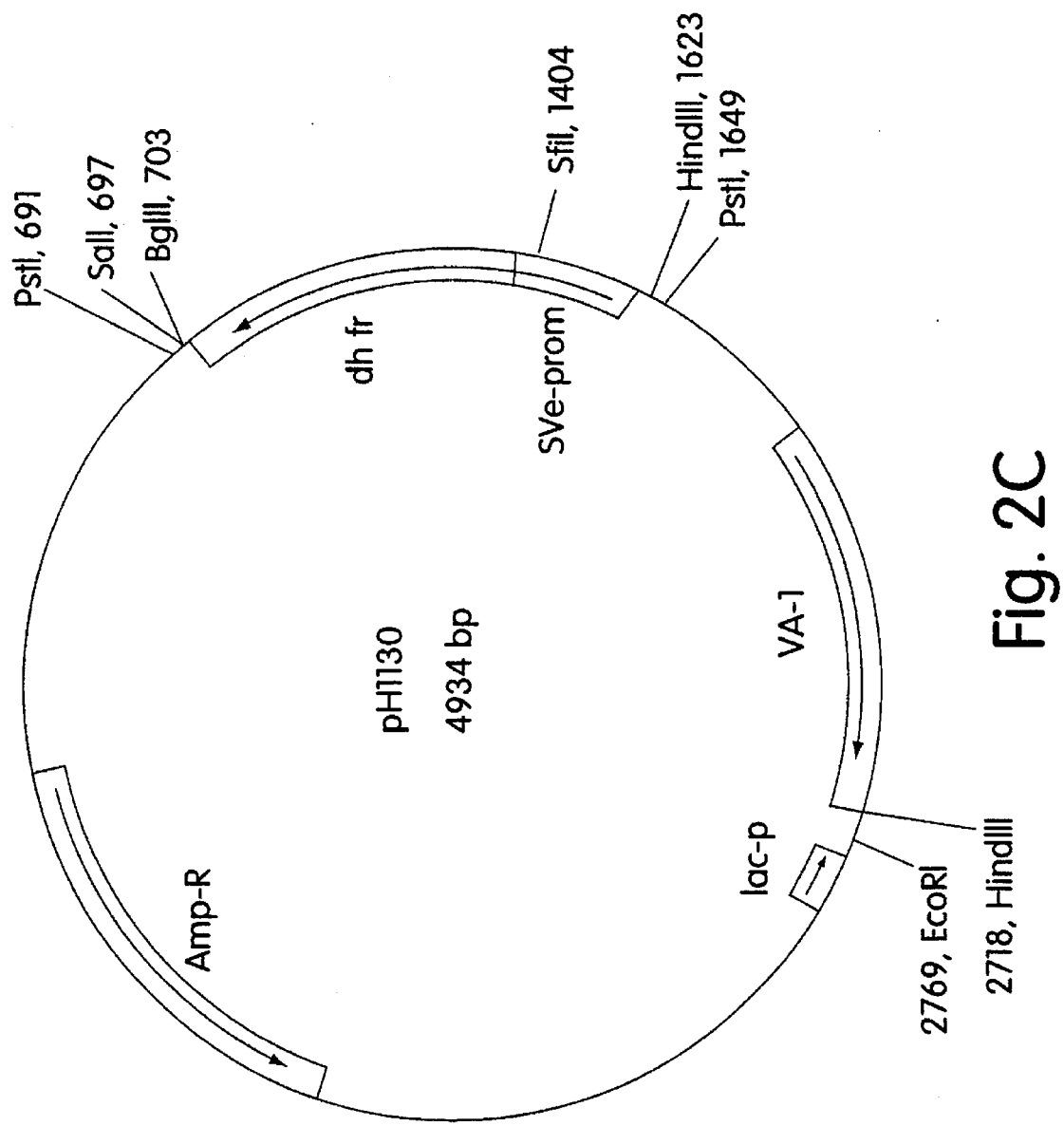

The pH989 (FIG. 2B) and pH1130 (FIG. 2C) vectors employ the adenovirus VA1 gene (Seq. ID No. 4) as a translation stimulator, e.g., an RNA sequence competent to promote translation of the transcript encoded by the gene of interest. Cloning of the adenovirus VA1 gene was achieved as follows: the VA1 and VA2 gene complex was isolated from adenovirus DNA by PCR using two synthetic oligonucleotides to gene terminal sequences (upper and lower strand, Seq. ID Nos. 5 and 6) and standard conditions for PCR. The primers added a new upstream PstI site and a downstream PvuII site. The PstI to PvuII fragment was cloned into the PstI and EcoRV sites of the SK(–) Bluescript cloning vector (Stratagene, Inc., Palo Alto, Calif.) resulting in plasmid pJ13 which was then incorporated into final vectors pH989 and pH1130 as follows.

In the case of pH989, the neo expression element from the pMam neo expression vector (Clontech, Inc.) was subcloned into the BamHI site of a standard pUC cloning vector, resulting in plasmid pH988. The plasmid orientation (with regard to the BamHI insert) in which the neo gene is colinear with the lac promoter of pUC was chosen for the next step, the addition of the VA1 gene. The VA1DNA was excised from pJ13 at flanking poly-linker sites, SpeI and ClaI, and the fragment was inserted between the XbaI and ClaI sites of the plasmid pH988 to yield pH989.

In the case of pH1130, a modified dhfr gene containing a minimal upstream untranslated region was constructed by site directed mutagenesis and a 5' PvuII site was introduced only a few nucleotides upstream of the ATG initiation condon. At the 3' end a SalI site was added next to a natural BglII site. Seq. ID No. 4 describes the nucleotide sequence of the Pst I-ECORI fragment of the pH1130 vector and includes both the VA gene sequence (e.g., nucleotides 1–1330) and the DHFR gene sequence.

The tailored dhfr gene was then inserted into plasmid pH989 in place of the neo gene. For this purpose pH989 was opened at a unique StuI site, located between the SV40 promoter and the neo gene, and at a unique SalI site, downstream or 3'of the neo gene and dhfr, as a PvuII to SalI fragment, was inserted. The end of PvuII and StuI sites are compatible for ligation and both sites are lost in the process. The resulting plasmid, pH1130, contains VA1 and dhfr.

EXAMPLE 2

Construction of Vectors for Single-chain Antibody Binding Site

The sFV genes described herein were cloned from cDNA libraries using appropriate probes as described in the art, or cloned by PCR using consensus primers.

sFV DNA sequences may be constructed either in the $V_H$-$V_L$ or $V_H$-$V_L$ configuration with a synthetic peptide linker cloned between the two elements as described in the art. Huston et al. (1993) *Inter. Rev. Immunol.* 10:195–217, incorporated herein above by reference, discloses a representative list of sFvs, as well as their parental monoclonals, their variable chain configuration, their linker length and composition, the antigens on which they act, and references wherein their construction is described.

An 741F8 sFv gene sequence was constructed as follows. The $V_H$ and $V_L$ genes of the 741F8 anti-c-erbB-2 monoclonal antibody were isolated from the cDNA of the parental 741F8 hybridoma line by PCR using primers homologous to the N-terminal coding regions of $V_H$, $V_L$, $C_H1$, and $C_L$. The PCR-amplified $V_H$ and $V_L$ genes were isolated by polyacrylamide gel electrophoresis and cloned into a pUC cloning vector. The first FR region of the 741F8 $V_H$ gene however contained spurious mutations due to the PCR procedure. Errors were rectified by the replacement of the first 70 nucleotides of 741F8 $V_H$ with a similar sequence from 520C9 $V_H$, another c-erbB-2 specific monoclonal antibody. Restriction sites were introduced into the ends of the 741F8 sequence (5'HindIII and 3'SalI sites) by site-directed mutagenesis (Kunkel et al., 1985, *Proc. Natl. Acad. Sci. USA* 82: 488–492) to incorporate the 741F8 sequence into a transfection vector. A stop codon at the C-terminal end of $V_L$ also was added. The gene construct contains a DNA sequence encoding a 14 residue polypeptide linker connecting the $V_H$ and $V_L$ domains. The sequence for 741F8 appears in Seq. ID Nos. 7 and 8. The sequence presented includes a C-terminal tail (Gly)$_4$-Cys, used in some constructs (see, Example 8). The sequence used in pH1512 does not include this tail sequence. Other forms of 741F8, e.g., wherein the orientation of $V_H$, $V_L$ are inverted, also were constructed and used with comparable success (see, Example 8).

As expression and secretion in mammalian cells requires a signal peptide sequence, a DNA sequence corresponding to the 520C9 monoclonal antibody heavy chain signal peptide (Seq. ID No. 9) was attached to the N-terminal sequence. Alternatively, the signal peptide sequence from other mammalian genes, preferably from other immunoglobulin genes may be used. As an example, the signal peptide sequence for Pac I is described in Seq. ID No.10.

Construction of the anti-digoxin 26–10 sFv has been described previously (Huston et al., 1988, *Proc. Natl. Acad. Sci. USA* 85; 5879–5883, and U.S. Pat. No. 5,091,513, both of which are hereby incorporated by reference).

The 520C9 sFv was generated by linking together the $V_H$ and $V_L$ genes, cloned from a 520C9 hybridoma cDNA library, with a serine rich linker. Briefly, the $V_H$ and $V_L$ genes were cloned from the 520C9 hybridoma cDNA library using probes directed toward the antibody constant (C) and joining (J) regions. Appropriate restriction sites were introduced at the ends of each gene by site-directed mutagenesis (Kunkel et al., 1985, *Proc. Natl. Acad. Sci. USA* 82: 488–492). The $V_H$ and $V_L$ genes were then ligated together with a serine rich linker.

The cDNA cloning, sequence, construction and expression of MOPC315 sFV in *E. coli* is disclosed in McCartney et al. (191) *J Protein Chem.*10: 669–683, the disclosure of which is incorporated herein by reference.

Several constructs also included C-terminal extensions either for ease of purification or to create bifunctional constructs. These extensions readily can be added by means of a serine rich spacer derived from a single-chain linker. In this manner, DNA seuences for a wide variety of extensions can be added, including genes for the FB fragment of protein A, for RNase S-peptide, and for Hexa-His (six histidine sequence) peptide. A hexa-histidine peptide is particularly useful for protein purification procedures as the sequence binds readily to an immobilized metal affinity chromatography ("IMAC") column.

Figure 3:
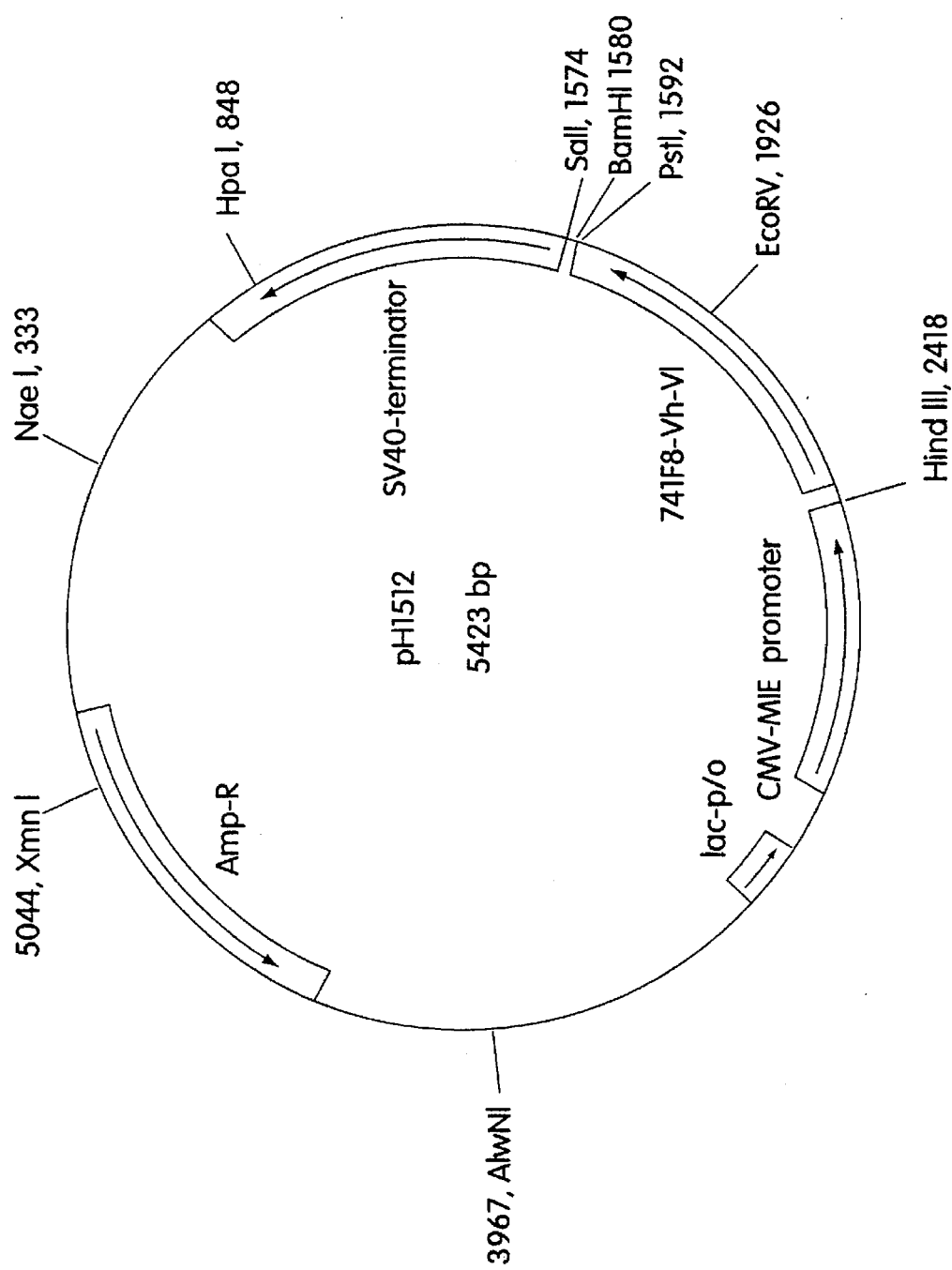
FIG. 3 is a restriction map of the exemplary vector pH 1512 carrying a DNA sequence encoding a single chain binding site as the non-native gene.

For expression of sFV molecules in mammalian cells, the CMV-MIE promoter/enhancer unit and SV40 terminator were employed. A 560 bp AseI to SacI fragment containing the immediate early promoter of cytomegalovirus (CMV) was cloned into the polylinker of a pUC vector (Stratagene, La Jolla, Calif.). Subsequently, the 3' mRNA processing signals were added: a fragment containing the SV40 early region splice signals and polyA additional signals was isolated as a 590 bp SalI to BamHI fragment from pMAM-neo (Clontech, Inc., Palo Alto, Calif.), yielding pH1512, FIG. 3. An alternative shorter 3'RNA processing signal contained in the HpaI to BamHI 150bp fragment of SV40 large T antigen has been used with comparable success.

EXAMPLE 3

Transfections

In all examples, transfections were by calcium phosphate coprecipitation, performed using standard procedures. CHO cells, DXB-11, from Dr. Lawrence Chasin, Columbia University, New York, were cultured in αMEM, containing 5% or 10% fetal bovine serum (FBS), non-essential amino acids, glutamine and antibiotics: penicillin and streptomycin, all obtained from GIBCO, New York. CHO cells transfected with vectors containing a neo gene were culture in the same growth medium containing the toxin G418 (0.4 mg/ml.) CHO cells transfected with vectors containing the DHFR selectable amplifiable gene, were cultured in α-MEM (αMEM lacking thymidine, glycine and hypoxanthine), 10% dialyzed FBS, and methotrexate (MTX) at 0.02–0.1 µM.

Stable cell line transfections were carried out by seeding 1–2×10$^6$ cells in a 9 cm. petri dish. Following up to 24-hour incubation in growth medium, each petri dish was transfected with 10–30 µg total vector DNA in equimolar amounts, by calcium phosphate coprecipitation followed by glycerol shock using standard methodology. Cells were incubated at 37° C. in growth medium for 24 hours, then transferred to selection medium. All cultures were fed once or twice weekly with fresh selective medium. After 10–21 days, resistant colonies were picked and assayed for protein production.

EXAMPLE 4

Selection Screening for Candidate Cell Lines

Following transfection and growth in selection medium, cells were screened for candidates to be subcloned, essentially as described in FIG. 1.

Briefly, individual clones from each transfection were selected, transferred to a 24-well petri dish, and allowed to grow to confluence in serum-containing media. The conditioned media from all surviving clones was screened for protein production using a standard ELISA (enzyme-linked immunosorbent assay) or Western blot. The methodologies for these assay protocols, as well as for generating antibodies for use in these assays are well described in the art (see, e.g., Ausubel). The parental monoclonals from which the sFvs are derived may be used to advantage.

EXAMPLE 5

Amplification/Sub-cloning/Cloning Methods

Candidate cell lines identified by the screening protocol of FIG. 1, then were seeded on ten 100 mm petri dishes at a cell density of either 50 or 100 cells per plate, and with a higher MTX concentration (e.g.,1.0–5µm).

After 10–21 days of growth, clones are isolated using cloning cylinders and standard procedures, and cultured in 24-well plates. Clones then were screened for protein production by Western immunoblots using standard procedures, and the protein levels compared to those of parental lines. Candidate cells showing higher protein production than cells of parental lines then were replated and grown in the presence of a still higher MTX concentration (e.g., 5–20µm). Generally, no more than 2–3 rounds of these "amplification" cloning steps is sufficient to achieve cells with high protein productivity. Useful high producing clones may be further subcloned to improve cell line homogeneity and product stability.

EXAMPLE 6

Characterization of Transfected Clone a) COPY NUMBER

Southern blots, using standard methodology, may be used to assess the state of integrated sequences and the extent of their copy number amplification in the host genome. Copy number experiments on various transfections are anticipated to indicate that the triple transfectants, fully amplified, have a low copy number of the artificial gene sequence (e.g., in the range of 1–50 copies), as compared with double or single transfectants that are not co-transfected with a transcription transactivating sequence.

b) mRNA MEASUREMENTS

Transcription levels of transfected artificial genes can be measured in the different expression systems by analyzing mRNA levels (Northern blots), using total cellular RNA and conventional hybridization methodology. Northern blots on various transfections are anticipated to indicate that transcript production is enhanced in double transfectants as compared with single transfectants, and still more enhanced in triple transfectants.

c) PROTEIN MEASUREMENTS

Protein levels were measured by Western blots (immunoblots) or ELISA, using standard methodologies and antisera against the protein product of interest. Western blot methodologies are well known to those skilled in the art, and may be performed using commercially-available reagents.

The protein data presented in Table I were produced in a "terminal" or "batch" culture of triply transfected CHO cells where protein was harvested when cells have reached post-logarithmic phase.

Protein production in Table I is represented by a relative scoring system ranging from a score of "−" (no detectable protein) to a score of "+++" (greater than or equal to 5 µg protein/$10^6$ cells/ml), wherein "+" is equivalent to less than about 1 µg/ml/$10^6$ cells. The data in Table I demonstrate that CHO cells triply transfected with the DNA sequences encoding artificial protein molecules are competent to produce high levels of protein, at least 1–5 ug/ml/$10^6$ cells in a batch culture in post-logarithmic phase. For example, using the triple transfection pH1512/pH1176/pH1130, clones producing at least 6.5 µg sFv protein/$10^6$ cells/ml were obtained. Also as indicated from the Table, the variable chain orientation and presence of terminal extensions has no apparent effect.

TABLE I

| Triple Transfection of sFv/E1A/Val in CHO CELLS | | | |
|---|---|---|---|
| PARENT MONOCLONAL/ (PLASMID) | SIGNAL PEPTIDE | CONSTRUCT STRUCTURE | Yield |
| 741F8 (pH 1424) | Pac1(K) | V1–Vh | +++ |
| MOPC315 (pH 1417) | 315(H) | Vh–V1 | ++ |
| 741F8 (pH 1517) | Pac1(K) | V1–Vh/6H | +++ |
| 741F8 (pH 1475) | 520C9 | Vh–V1 (ser-cys) | ++ |

These data demonstrate that the invention's combination of transfecting DNA sequences is suitable for the production of useful quantities of proteins encoded by non-native sequences, particularly single chain-binding site constructs.

EXAMPLE 7

General Isolation/Purification Scheme

The sFv polypeptide chains can be purified as described in the art. For example, ouabain-Sepharose affinity chromatography has been described for the 26-10 sFv constructs (Huston, et. al., 1988, *Proc. Natl Acad. Sci. USA* 85; 5879–5883 and Tai, et al., 1990, *Biochem.* 29, 8024–3080, both of which are hereby incorporated by reference). The folded 520C9 and 741F8 SFv polypeptide chains similarly can be purified using a c-erbB-2-agarose affinity column. For example, the samples are loaded onto a c-erbB-2 affinity column, the column washed with PBS, and the sFv polypeptides eluted with PBS pH 6.1 containing 3M LiCl. The buffer then is exchanged by dialysis. The c-erbB-2 affinity column preferably is prepared by linking the extracellular domain of c-erbB-2 onto agarose beads and as described below.

Briefly, the c-erbB-2 sequence coding for its extracellular domain (ECD) was derived from the baculovirus expression vector described previously (Ring et al., 1992, *Mol. Immunol.* 28; 915–917). A DNA duplex encoding the $His_6$ peptide was ligated to the 3' end of the ECD gene, and the construct expressed in CHO cells. The ECD polypeptide was purified from the CHO cell culture medium on an IMAC metal affinity column (Pharmacia, Piscataway, N.J.), as described in Skerra, et al., 1991, *Bio/Technology* 9: 273–278, and the eluted ECD proteins attached onto agarose beads to generate the c-erbB-2-agarose affinity resin.

Similarly, other sFvs may be purified by immunoaffinity chromatography using, for example, the parent monoclonal antibody as part of the affinity matrix. Alternatively, terminal extension sequences may be include which encode protein sequences that aid in purification. For example a Hexa-His sequence, (6 histidine residues), has particular affinity for IMAC chromatography. Where the terminal extension is part of the FB peptide, the immunoadsorbent column may comprise staphylococus protein A; where the terminal extension comprises S-peptide, the immunosorbent column can contain S-protein-Sepharose.

EXAMPLE 8

SFv Protein Production in a Transient Cells System

As a preliminary screen of vector contructs, a number of sFv genetic sequences were transfected into an E1A-expressing cell line (293 cells, human embryonic kidney cells expressing at least the E1A gene of adenovirus-2) were co-transfected with particular sFv constructs and with VA1 gene sequences. Cells were transfected as described above, and screened for protein production. Table II summarizes the results of a transient cell system using 293 cells to produce single chain binding sites. In the table the sFv construct structures are described, including the orientation of the variable region sequences, and any C-terminal extensions. Such a system is useful to screen the expression efficacy of certain DNA sequences encoding single chain proteins, as well as to screen the efficacy of particular transfection combinations. The data in Table II, moreover, illustrate the general utility of the invention's transfection strategy for the production of high levels of protein from poorly expressed DNA sequences in mammalian cells.

As described above, protein production is depicted by a relative scoring system where "+++" represents detection of at least about 5 µg protein/ml; and "++" represents detection of at least 1 µg protein/ml. Generally speaking, triple transfectants scored at least "++" levels of protein production, and approximately 50% scored +++ levels. Again, these data illustrate the utility of the invention's transfection strategy to produce high levels of recombinant, non-native protein from a variety of DNA constructs.

Candidate vectors, e.g., vectors and vector combinations which, when transfected into 293 cells produced at least a "++" (detectable quantities of protein to about 1 µg/ml) now can be transfected into. Similar transfections will be conducted using immortalized host cells such as CHO cells, in which it is anticipated that the actual utility of these constructs for long term cell growth will be confirmed, and protein production data similar to those in Table I will be obtained.

TABLE II

| PARENT MONOCLONAL/ (Plasmid) | SIGNAL PEPTIDE | STRUCTURE | Yield |
|---|---|---|---|
| 293 CELLS | | | |
| 741F8 (pH 4424) | Pac1 | V1–Vh | ++ |
| 741F8 (pH 1524) | 520C9 | Vh–V1 [GGGGS × 3] | +++ |
| 741F8 (pH 1512) | 520C9 | Vh–V1 [DP] | +++ |
| MOPC315 (pH 1417) | 315 | Vh–V1 | ++ |
| 741F8 (pH 1517) | Pac1 | V1–Vh/(His$_6$) | +++ |
| 741F8 (pH 1529) | Pac1 | V1–Vh/(His$_6$) | ++ |
| 741F8 (pH 1467) | 520C9 | Vh–V1/(S-pept.) | +++ |
| 741F8 (pH 1510) | 520C9 | Vh–V1/FB | +++ |
| 741F8 (pH 1603) | 520C9 | Vh–V1/IL2 | +++ |
| 520C9(Vh) (pH 1547) | 520C9 | Vh–V1/FB | ++ |

TABLE II-continued

| PARENT MONOCLONAL/ (Plasmid) | SIGNAL PEPTIDE | STRUCTURE | Yield |
|---|---|---|---|
| 293 CELLS | | | |
| 741F8(V1) 741F8(Vh) (pH 1515) 26–10(V1) | 520C9 | Vh–V1 | +++ |
| 741F8 (pH 1476) | 520C9 | Vh–V1/gly4-cys | + |
| 741F8 (pH 1478) | 520C9 | Vh–V1/ser-cys | ++ |

EXAMPLE 9

Transfected Myeloma SP2/0 Cells

As a further means of testing the general utility of non-native DNA sequences and certain transfection methodologies, myeloma SP2/0 cells were triply transfected, using the transfection and screening protocols described herein. All plasmids were constructed using standard procedures, reasonable quantities (at least 1–5 µg/ml) were obtained. As described in Table III, all triple transfections using sFv co-transfected with E1A (pH1176) and VA1 (pH1130 or pH989). Reasonable quantities (at least 1–5 µg protein/ml) were obtained.

TABLE III

| PARENT MONOCLONAL/ (PLASMID) | SIGNAL PEPTIDE | STRUCTURE | Yield |
|---|---|---|---|
| SP2/0 CELLS | | | |
| 741F8 (pH 1327) | Pac1 K | V1–Vh | +++ |
| 741F8 (pH 1339) | Pac1 K | V1–Vh | ++ |
| MOPC315 (pH 1428) | 315 H | Vh–V1 | +++ |

The data in Table III yet again confirm the general utility of the invention's transfection strategies for a variety of mammalian host cells.

EXAMPLE 10

V.protein Production in Large Scale Protocols

A currently preferred method of large scale protein production e.g., at least 2 liter, is by suspension culturing of the host CHO cells. Chinese hamster ovary cells are attachment preferred but can be adapted to grow in suspension mode of cultivation. The cells are trypsinized from the dish, introduced to growth media containing 10% FBS and using a pipet, completely suspended to ideally achieve a single cell suspension. This is introduced to a spinner flask and placed in a 37° C.95%/air/5% $CO_2$ humidified incubator. Over a period of time the cells are subcultured in medium with descending concentrations of serum. Within the spinner flasks there is a balance between sufficient agitation rate to maintain a single cell suspension and the shear force associated with the agitation impeller. Due to the nature of 95%air/5% $CO_2$ incubators there is a balance between oxygen absorption/$CO_2$ desorbtion in the medium and agitation rate, as well as, surface to volume ratios.

For example, the production of CHO conditioned medium in suspension cultures is carried out as follows: The adapted cells are introduced into a 3 L spinner flask at an initial viable cell density of approximately $2 \times 10^5$ cells/ml. The culture medium is DMEM/F-12 (1:1) (GIBCO, New York) supplemented with 2% FBS. The agitation was approximately 50–60 rpm with a paddle impeller. The culture volume was 1500 mls (half max.) in order to increase relative surface to volume ratio. After 7 days the culture media is harvested, centrifuged at 1500 rpm and the clarified conditioned media stored at 4°.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A method of manufacturing a cell line for the enhanced production of a biosynthetic single chain binding protein, the method comprising the steps of:
    (a) transfecting an immortalized eukaryotic cell with a nucleic acid comprising a DNA sequence encoding a viral transcription activator protein that acts on and stimulates a viral promoter, wherein said DNA sequence encoding said viral transcription activator protein is operatively associated with, and under the control of, a DNA sequence defining a transcription promoter sequence which can induce transcription of said viral transcription activator protein DNA sequence, said transcription promoter DNA sequence being selected to permit unlimited or limited transcription of said viral transcription activator protein DNA sequence;
    (b) transfecting said immortalized eukaryotic cell with nucleic acids comprising:
        (1) a DNA sequence encoding a viral transcription promoter operatively associated with a non-native reporter DNA sequence encoding a biosynthetic single chain binding protein, said viral transcription promoter capable of being stimulated by said viral transcription activator protein, and competent to act on and induce transcription of said reporter DNA sequence to produce an RNA transcript, said transcript, when translated, producing a single-chain binding protein that, when properly folded, has a structural conformation capable of mono- or bifunctional binding activity; and
        (2) a DNA sequence encoding an RNA sequence, said RNA sequence promoting translation of said RNA transcript from step (b)(1) above;
    (c) culturing said transfected cell under conditions that allow said transfected cell to integrate into its genome said DNA sequences such that said integration permits growth of said cell and production of said single-chain binding protein, said protein being produced at a level greater than if said cell is transfected with said reporter DNA sequence alone or in combination with only one of the DNA sequences of step (a) or (b)(2) above; and
    (d) identifying a clone of said cultured transfected cell of step (c) that expresses at least 1 μg single-chain binding proteins/$10^6$ cell/ml.

2. The method of claim 1 wherein the transfecting steps (a) and (b) are performed simultaneously.

3. The method of claim 1 wherein the transfecting steps (a) and (b) are performed sequentially.

4. The method of claim 1 wherein said DNA sequence encoding said viral transcription activator protein is stably integrated into the genome of said cell before the transfecting of step (b).

5. The method of claim 1 wherein said DNA sequence encoding said RNA sequence comprises part of a nucleic acid separate and independent of a nucleic acid comprising said DNA sequence encoding said viral promoter operatively associated with said reporter DNA sequence encoding said biosynthetic single-chain binding protein.

6. The method of claims 1 wherein said nucleic acids comprise independent vectors.

7. The method of manufacture of claim 1 wherein said DNA sequences transfected in steps (a) and (b) are stably integrated into the genome of the clone selected in step (d).

8. The method of manufacture of claim 1 wherein the copy number of said non-native reporter DNA sequence encoding said biosynthetic single-chain binding protein and integrated into the genome of said cell is less than 20 copies per cell.

9. The method of manufacture of claim 1 wherein said copy number of said non-native reporter DNA sequence is less than 10 copies per cell.

10. The method of manufacture of claim 1 wherein said copy number of said non-native reporter DNA sequence is less than 5 copies per cell.

11. The method of manufacture of claim 1 wherein said viral transcription promoter is selected from the group consisting of promoters derived from simian virus 40, adenovirus, rous sarcomavirus, and cytomegalovirus.

12. The method of manufacture of claim 1 wherein said viral transcription promoter comprises the constitutive major intermediate-early promoter of cytomegalovirus.

13. The method of manufacture of claim 1 wherein said transcription activator protein is a viral transactivating protein competent to act on and stimulate transcription of a non-native gene.

14. The method of manufacture of claim 1 wherein said viral transcription activator protein is selected from the group consisting of simian virus T antigen, adenovirus E1A or E1B protein, and herpesvirus IE proteins.

15. The method of manufacture of claim 1 wherein said transcription activator protein is E1A.

16. The method of manufacture of claim 27 wherein said transcription promoter DNA sequence is selected to limit transcription of said viral transcription activator DNA sequence.

17. The method of manufacture of claim 1 wherein said RNA sequence is a transactivating RNA sequence of viral origin, competent to act on and enhance translation of an RNA transcript encoded by a non-native gene.

18. The method of manufacture of claim 1 wherein said RNA sequence is selected from the group consisting of the adenovirus VA1 RNA, and an RNA sequence encoded by the bovine papilloma virus early region DNA.

19. The method of manufacture of claim 1 wherein said RNA sequence is VA1.

20. The method of manufacture of claim 1 wherein said biosynthetic single-chain binding protein is a protein selected from the group consisting of mono- or bifunctional single-chain antibody binding sites.

21. The method of manufacture of claim 1 wherein said non-native reporter DNA sequence encoding said biosynthetic single-chain binding protein encodes the binding site for c-erbB2/HER-2 antigen.

22. The method of manufacture of claim 1 wherein said non-native reporter DNA sequence encoding said biosynthetic single-chain binding protein encodes MOPC315 myeloma antibody binding site.

23. The method of manufacture of claim 1 wherein said cell is a Chinese hamster ovary cell.

24. The method of manufacture of claim 1 further comprising means for amplifying the copy number of said non-native reporter DNA sequence encoding said biosynthetic single-chain binding protein.

25. The method of manufacture of claim 1 wherein said amplification means comprises a sequence DNA encoding dihydrofolate reductase (DHFR) in operative association with a promoter sequence that acts on and induces transcription of said DHFR DNA.

26. The method of manufacture of claim 1 comprising the additional steps of:

(a) culturing said clone under conditions sufficient to produce a population of said clones expressing said single-chain binding protein; and (b) isolating said single-chain binding protein from the culture media.

* * * * *

UNITED STATES PATENT AND TRADEMARK OFFICE
CERTIFICATE OF CORRECTION

PATENT NO.  : 5,631,158
DATED       : May 20, 1997
INVENTOR(S) : Dorai et al.

It is certified that error appears in the above-identified patent and that said Letters Patent is hereby corrected as shown below:

On the cover sheet, in the text following "[*] Notice:", after "subsequent to," delete "Oct. 25, 2013" and insert -- Dec. 17, 2013 --.

Signed and Sealed this

Twenty-eighth Day of October, 1997

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
       ( A ) LENGTH: 1356 base pairs
       ( B ) TYPE: nucleic acid
       ( C ) STRANDEDNESS: single
       ( D ) TOPOLOGY: linear ( i i ) MOLECULE TYPE: cDNA ( i x ) FEATURE:
       ( A ) NAME/KEY: misc_feature
       ( B ) LOCATION: 1..1356
       ( C ) OTHER INFORMATION: /note= "adeE1A"

( x i ) SEQUENCE DESCRIPTION: SEQ ID NO: 1:

| | | | | | | |
|---|---|---|---|---|---|---|
| CTGCAGGTCC | TGCTTCATCC | CCGTGGCCCG | TTGCTCGCGT | TTGCTGGCGG | TGTCCCGGA | 60 |
| AGAAATATAT | TTGCATGTCT | TTAGTTCTAT | GATGACACAA | ACCCCGCCCA | GCGTCTTGTC | 120 |
| ATTGGCGAAT | TCGAACACGC | AGATGCAGTC | GGGGCGGCGC | GGTCCCAGGT | CCACTTCGCA | 180 |
| TATTAAGGTG | ACGCGTGTGG | CCTCGAACAC | CGAGCGACCC | TGCAGCGACC | CGCTTAACAG | 240 |
| CGTCCCTCCA | TGAGACATAT | TATCTGCCAC | GGAGGTGTTA | TTACCGAAGA | AATGGCCGCC | 300 |
| AGTCTTTTGG | ACCAGCTGAT | CGAAGAGGTA | CTGGCTGATA | ATCTTCCACC | TCCTAGCCAT | 360 |
| TTTGAACCAC | CTACCCTTCA | CGAACTGTAT | GATTTAGACG | TGACGGCCCC | CGAAGATCCC | 420 |
| AACGAGGAGG | CGGTTTCGCA | GATTTTTCCC | GAGTCTGTAA | TGTTGGCGGT | GCAGGAAGGG | 480 |
| ATTGACTTAT | TCACTTTTCC | GCCGGCGCCC | GGTTCTCCGG | AGCCGCCTCA | CCTTTCCCGG | 540 |
| CAGCCCGAGC | AGCCGGAGCA | GAGAGCCTTG | GGTCCGGTTT | CTATGCCAAA | CCTTGTGCCG | 600 |
| GAGGTGATCG | ATCTTACCTG | CCACGAGGCT | GGCTTTCCAC | CCAGTGACGA | CGAGGATGAA | 660 |
| GAGGGTGAGG | AGTTTGTGTT | AGATTATGTG | GAGCACCCCG | GGCACGGTTG | CAGGTCTTGT | 720 |
| CATTATCACC | GGAGGAATAC | GGGGGACCCA | GATATTATGT | GTTCGCTTTG | CTATATGAGG | 780 |
| ACCTGTGGCA | TGTTTGTCTA | CAGTAAGTGA | AAATTATGGG | CAGTCGGTGA | TAGAGTGGTG | 840 |
| GGTTTGGTGT | GGTAATTTTT | TTTTAATTTT | TACAGTTTTG | TGGTTTAAAG | AATTTTGTAT | 900 |
| TGTGATTTTT | TAAAAGGTCC | TGTGTCTGAA | CCTGAGCCTG | AGCCCGAGCC | AGAACGGAG | 960 |
| CCTGCAAGAC | CTACCCGGCG | TCCTAAATTG | GTGCCTGCTA | TCCTGAGACG | CCCGACATCA | 1020 |
| CCTGTGTCTA | GAGAATGCAA | TAGTAGTACG | GATAGCTGTG | ACTCCGGTCC | TTCTAACACA | 1080 |
| CCTCCTGAGA | TACACCCGGT | GGTCCCGCTG | TGCCCATTA | AACCAGTTGC | CGTGAGAGTT | 1140 |
| GGTGGGCGTC | GCCAGGCTGT | GGAATGTATC | GAGGACTTGC | TTAACGAGTC | TGGGCAACCT | 1200 |
| TTGGACTTGA | GCTGTAAACG | CCCCAGGCCA | TAAGGTGTAA | ACCTGTGATT | GCGTGTGTGG | 1260 |
| TTAACGCCTT | TGTTTGCTGA | ATGAGTTGAT | GTAAGTTTAA | TAAAGGGTGA | GATAATGTTT | 1320 |

AACTTGCATG GCGTGTTAAA TGGGGCGGGG AGATCT                                              1356

( 2 ) INFORMATION FOR SEQ ID NO: 2:

( i ) SEQUENCE CHARACTERISTICS:
        ( A ) LENGTH: 36 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..36
        ( C ) OTHER INFORMATION: /note= "E1Aprim1"

( x i ) SEQUENCE DESCRIPTION: SEQ ID NO: 2:

AAAGGCCTCC ATGAGACATA TTATCTGCCA CGGAGG                                              36

( 2 ) INFORMATION FOR SEQ ID NO: 3:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..28
        ( C ) OTHER INFORMATION: /note= "E1Aprim2"

( x i ) SEQUENCE DESCRIPTION: SEQ ID NO: 3:

AAAGATCTCC CCATTTAACA CGCCATGC                                                       28

( 2 ) INFORMATION FOR SEQ ID NO: 4:

( i ) SEQUENCE CHARACTERISTICS:
        ( A ) LENGTH: 2037 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..2037
        ( C ) OTHER INFORMATION: /note= "adeVA1"

( x i ) SEQUENCE DESCRIPTION: SEQ ID NO: 4:

AAGCTTGATC TGCACCCTTG GGTGTCGCTC AGGAGAGGGC GCTCCTAGCC GCGCCAGGCC                    60

CTCGCCCTCC TCCAAGTCCA GGTAGTGCCG GGCCCGGCGC CGCGGGGGTT CGTAATCACC                    120

ATCTGCCGCC GCGTCAGCCG CGGATGTTGC CCCTCCTGAC GCGGTAGGAG AAGGGGAGGG                    180

TGCCCTGCAT GTCTGCCGCT GCTCTTGCTC TTGCCGCTGC TGAGGAGGGG GGCGCATCTG                    240

CCGCAGCACC GGATGCATCT GGGAAAAGCA AAAAGGGGC TCGTCCCTGT TTCCGGAGGA                     300

ATTTGCAAGC GGGGTCTTGC ATGACGGGA GGCAAACCCC CGTTCGCCGC AGTCCGGCCG                     360

GCCCGAGACT CGAACCGGGG GTCCTGCGAC TCAACCCTTG GAAAATAACC CTCCGGCTAC                    420

AGGGAGCGAG CCACTTAATG CTTTCGCTTT CCAGCCTAAC CGCTTACGCC GCGCGCGGCC                    480

AGTGGCCAAA AAAGCTAGCG CAGCAGCCGC CGCGCCTGGA AGGAAGCCAA AAGGAGCGCT                    540

CCCCCGTTGT CTGACGTCGC ACACCTGGGT TCGACACGCG GGCGGTAACC GCATGGATCA                    600

| | | | | | |
|---|---|---|---|---|---|
|CGGCGGACGG|CCGGATCCGG|GGTTCGAACC|CCGGTCGTCC|GCCATGATAC|CCTTGCGAAT|660|
|TTATCCACCA|GACCACGGAA|GAGTGCCCGC|TTACAGGCTC|TCCTTTTGCA|CGGTCTAGAG|720|
|CGTCAACGAC|TGCGCACGCC|TCACCGGCCA|GAGCGTCCCG|ACCATGGAGC|ACTTTTTGCC|780|
|GCTGCGCAAC|ATCTGGAACC|GCGTCCGCGA|CTTTCCGCGC|GCCTCCACCA|CCGCCGCCGG|840|
|CATCACCTGG|ATGTCCAGGT|ACATCTACGG|ATATCATCGC|CTTATGTTGG|AAGACCTCGC|900|
|CCCCGGAGCC|CCGGCCACCC|TACGCTGGCC|CCTCTACCGC|CAGCCGCCGC|CGCACTTTTT|960|
|GGTGGGATAT|CAGTACCTGG|TGCGGACTTG|CAACGACTAC|GTCTTTGACT|CAAGGGCTTA|1020|
|CTCGCGTCTC|AGGTACACCG|AGCTCTCGCA|GCCGGGTCAC|CAGACCGTTA|ACTGGTCGTT|1080|
|ATGGCCAACT|GCAGCCCGGG|GGATCCACTA|GAAGAAGCTT|GGGATCCGGC|TGTGGAATGT|1140|
|GTGTCAGTTA|GGGTGTGGAA|AGTCCCCAGG|CTCCCAGCA|GGCAGAAGTA|TGCAAAGCAT|1200|
|GCATCTCAAC|CAGACAGCAA|CCATAGTCCC|TCCCTAACT|CCGCCCATCC|CGCCCCTAAC|1260|
|TCCGCCCAGT|TCCGCCCATT|CTCCGCCCCA|TGGCTGACTA|ATTTTTTTA|TTTATGCAGA|1320|
|GGCCGAGGCC|GCCTCGGCCT|CTGAGCTATT|CCAGAAGTAG|TGAGGAGGCT|TTTTGGAGG|1380|
|CTGCCATCAT|GGTTCGACCA|TTGAACTGCA|TCGTCGCCGT|GTCCCAAAAT|ATGGGGATTG|1440|
|GCAAGAACGG|AGACCTACCC|TGGCCTCCGC|TCAGGAACGA|GTTCAAGTAC|TTCCAAAGAA|1500|
|TGACCACAAC|CTCTTCAGTG|GAAGGTAAAC|AGAATCTGGT|GATTATGGGT|AGGAAAACCT|1560|
|GGTTCTCCAT|TCCTGAGAAG|AATCGACCTT|TAAAGGACAG|AATTAATATA|GTTCTCAGTA|1620|
|GAGAACTCAA|AGAACCACCA|CGAGGAGCTC|ATTTCTTGC|CAAAAGTTTG|GATGATGCCT|1680|
|TAAGACTTAT|TGAACAACCG|GAATTGGCAA|GTAAAGTAGA|CATGGTTTGG|ATAGTCGGAG|1740|
|GCAGTTCTGT|TTACCAGGAA|GCCATGAATC|AACCAGGCCA|CCTCAGACTC|TTTGTGACAA|1800|
|GGATCATGCA|GGAATTTGAA|AGTGACACGT|TTTTCCCAGA|AATTGATTTG|GGGAAATATA|1860|
|AACTTCTCCC|AGAATACCCA|GGCGTCCTCT|CTGAGGTCCA|GGAGGAAAAA|GGCATCAAGT|1920|
|CTAAGTTTGA|AGTCTACGAG|AAGAAAGACT|AACAGGAAGA|TGCTTTCAAG|TTCTCTGCTC|1980|
|CCCTCCTAAA|GCTATGCATT|TTTATAAGAC|CATGGGACTT|TTGCTGGCTT|TAGATCT|2037|

( 2 ) INFORMATION FOR SEQ ID NO: 5:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..22
        ( C ) OTHER INFORMATION: /note= "VA1prim1"

( x i ) SEQUENCE DESCRIPTION: SEQ ID NO: 5:

CCGACTGCAG TTGGCCATAA CG        22

( 2 ) INFORMATION FOR SEQ ID NO: 6:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
   ( A ) NAME/KEY: misc_feature
   ( B ) LOCATION: 1..23
   ( C ) OTHER INFORMATION: /note= "VA1prim2"

( x i ) SEQUENCE DESCRIPTION: SEQ ID NO: 6:

GGCACGCTTC AGCTGCACCC TTG                                                  23

( 2 ) INFORMATION FOR SEQ ID NO: 7:

( i ) SEQUENCE CHARACTERISTICS:
      ( A ) LENGTH: 909 base pairs
      ( B ) TYPE: nucleic acid
      ( C ) STRANDEDNESS: single
      ( D ) TOPOLOGY: linear ( i i ) MOLECULE TYPE: cDNA ( i x ) FEATURE:
      ( A ) NAME/KEY: CDS
      ( B ) LOCATION: 3..752
      ( D ) OTHER INFORMATION: /product="741F8 sFv'"

( x i ) SEQUENCE DESCRIPTION: SEQ ID NO: 7:

| | | | | | | | | | | | | | | | | |
|---|---|---|---|---|---|---|---|---|---|---|---|---|---|---|---|---|---|
| CC | ATG | GCG | GAG | ATC | CAA | TTG | GTG | CAG | TCT | GGA | CCT | GAG | CTG | AAG | AAG | | 47 |
| | Met | Ala | Glu | Ile | Gln | Leu | Val | Gln | Ser | Gly | Pro | Glu | Leu | Lys | Lys | | |
| | 1 | | | | 5 | | | | | 10 | | | | | 15 | | |
| CCT | GGA | GAG | ACA | GTC | AAG | ATC | TCC | TGC | AAG | GCT | TCT | GGG | TAT | ACC | TTC | | 95 |
| Pro | Gly | Glu | Thr | Val | Lys | Ile | Ser | Cys | Lys | Ala | Ser | Gly | Tyr | Thr | Phe | | |
| | | | | 20 | | | | | 25 | | | | | 30 | | | |
| ACA | AAC | TAT | GGA | ATG | AAC | TGG | GTG | AAG | CAG | GCT | CCA | GGA | AAG | GGT | TTA | | 143 |
| Thr | Asn | Tyr | Gly | Met | Asn | Trp | Val | Lys | Gln | Ala | Pro | Gly | Lys | Gly | Leu | | |
| | | | 35 | | | | 40 | | | | | 45 | | | | | |
| AAG | TGG | ATG | GGC | TGG | ATA | AAC | ACC | AAC | ACT | GGA | GAG | CCA | ACA | TAT | GCT | | 191 |
| Lys | Trp | Met | Gly | Trp | Ile | Asn | Thr | Asn | Thr | Gly | Glu | Pro | Thr | Tyr | Ala | | |
| | | 50 | | | | 55 | | | | | 60 | | | | | | |
| GAA | GAG | TTC | AAG | GGA | CGG | TTT | GCC | TTC | TCT | TTG | GAA | ACC | TCT | GCC | AGC | | 239 |
| Glu | Glu | Phe | Lys | Gly | Arg | Phe | Ala | Phe | Ser | Leu | Glu | Thr | Ser | Ala | Ser | | |
| | 65 | | | | 70 | | | | | 75 | | | | | | | |
| ACT | GCC | TAT | TTG | CAG | ATC | AAC | AAC | CTC | AAA | AAT | GAG | GAC | ACG | GCT | ACA | | 287 |
| Thr | Ala | Tyr | Leu | Gln | Ile | Asn | Asn | Leu | Lys | Asn | Glu | Asp | Thr | Ala | Thr | | |
| 80 | | | | | 85 | | | | | 90 | | | | | 95 | | |
| TAT | TTC | TGT | GGA | AGG | CAA | TTT | ATT | ACC | TAC | GGC | GGG | TTT | GCT | AAC | TGG | | 335 |
| Tyr | Phe | Cys | Gly | Arg | Gln | Phe | Ile | Thr | Tyr | Gly | Gly | Phe | Ala | Asn | Trp | | |
| | | | 100 | | | | | 105 | | | | | 110 | | | | |
| GGC | CAA | GGG | ACT | CTG | GTC | ACT | GTC | TCT | GCA | TCG | AGC | TCC | TCC | GGA | TCT | | 383 |
| Gly | Gln | Gly | Thr | Leu | Val | Thr | Val | Ser | Ala | Ser | Ser | Ser | Ser | Gly | Ser | | |
| | | | 115 | | | | 120 | | | | | 125 | | | | | |
| TCA | TCT | AGC | GGT | TCC | AGC | TCG | AGC | GAT | ATC | GTC | ATG | ACC | CAG | TCT | CCT | | 431 |
| Ser | Ser | Ser | Gly | Ser | Ser | Ser | Ser | Asp | Ile | Val | Met | Thr | Gln | Ser | Pro | | |
| | | 130 | | | | 135 | | | | | 140 | | | | | | |
| AAA | TTC | ATG | TCC | ACG | TCA | GTG | GGA | GAC | AGG | GTC | AGC | ATC | TCC | TGC | AAG | | 479 |
| Lys | Phe | Met | Ser | Thr | Ser | Val | Gly | Asp | Arg | Val | Ser | Ile | Ser | Cys | Lys | | |
| | 145 | | | | 150 | | | | | 155 | | | | | | | |
| GCC | AGT | CAG | GAT | GTG | AGT | ACT | GCT | GTA | GCC | TGG | TAT | CAA | CAA | AAA | CCA | | 527 |
| Ala | Ser | Gln | Asp | Val | Ser | Thr | Ala | Val | Ala | Trp | Tyr | Gln | Gln | Lys | Pro | | |
| 160 | | | | | 165 | | | | | 170 | | | | | 175 | | |
| GGG | CAA | TCT | CCT | AAA | CTA | CTG | ATT | TAC | TGG | ACA | TCC | ACC | CGG | CAC | ACT | | 575 |
| Gly | Gln | Ser | Pro | Lys | Leu | Leu | Ile | Tyr | Trp | Thr | Ser | Thr | Arg | His | Thr | | |
| | | | | 180 | | | | | 185 | | | | | 190 | | | |
| GGA | GTC | CCT | GAT | CGC | TTC | ACA | GGC | AGT | GGA | TCT | GGG | ACA | GAT | TAT | ACT | | 623 |
| Gly | Val | Pro | Asp | Arg | Phe | Thr | Gly | Ser | Gly | Ser | Gly | Thr | Asp | Tyr | Thr | | |
| | | | 195 | | | | | 200 | | | | | 205 | | | | |
| CTC | ACC | ATC | AGC | AGT | GTG | CAG | GCT | GAA | GAC | CTG | GCA | CTT | CAT | TAC | TGT | | 671 |

```
Leu Thr Ile Ser Ser Val Gln Ala Glu Asp Leu Ala Leu His Tyr Cys
        210                 215                 220

CAG CAA CAT TAT AGA GTG CCG TAC ACG TTC GGA GGG GGG ACC AAG CTG         719
Gln Gln His Tyr Arg Val Pro Tyr Thr Phe Gly Gly Gly Thr Lys Leu
    225                 230                 235

GAG ATA AAA CGG GCT GAT GGG GGA GGT GGA TGT TAACGGGGA GGTGGATGTT        772
Glu Ile Lys Arg Ala Asp Gly Gly Gly Gly Cys
240                 245                 250

GGGTCTCGTT ACGTTGCGGA TCTCGAGGCT ATCTTTACTA ACTCTTACCG TAAAGTTCTG       832

GCTCAACTGT CTGCACGCAA GCTTTTGCAG GATATCATGA GCGCTTAAGA TCCGTCGACC       892

TGCAGGCATG CAAGCTT                                                      909
```

( 2 ) INFORMATION FOR SEQ ID NO: 8:

( i ) SEQUENCE CHARACTERISTICS:
        ( A ) LENGTH: 250 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

```
Met Ala Glu Ile Gln Leu Val Gln Ser Gly Pro Glu Leu Lys Lys Pro
1                   5                   10                  15

Gly Glu Thr Val Lys Ile Ser Cys Lys Ala Ser Gly Tyr Thr Phe Thr
                20                  25                  30

Asn Tyr Gly Met Asn Trp Val Lys Gln Ala Pro Gly Lys Gly Leu Lys
            35                  40                  45

Trp Met Gly Trp Ile Asn Thr Asn Thr Gly Glu Pro Thr Tyr Ala Glu
    50                  55                  60

Glu Phe Lys Gly Arg Phe Ala Phe Ser Leu Glu Thr Ser Ala Ser Thr
65                  70                  75                  80

Ala Tyr Leu Gln Ile Asn Asn Leu Lys Asn Glu Asp Thr Ala Thr Tyr
                85                  90                  95

Phe Cys Gly Arg Gln Phe Ile Thr Tyr Gly Gly Phe Ala Asn Trp Gly
            100                 105                 110

Gln Gly Thr Leu Val Thr Val Ser Ala Ser Ser Ser Ser Gly Ser Ser
    115                 120                 125

Ser Ser Gly Ser Ser Ser Asp Ile Val Met Thr Gln Ser Pro Lys
130                 135                 140

Phe Met Ser Thr Ser Val Gly Asp Arg Val Ser Ile Ser Cys Lys Ala
145                 150                 155                 160

Ser Gln Asp Val Ser Thr Ala Val Ala Trp Tyr Gln Gln Lys Pro Gly
                165                 170                 175

Gln Ser Pro Lys Leu Leu Ile Tyr Trp Thr Ser Thr Arg His Thr Gly
            180                 185                 190

Val Pro Asp Arg Phe Thr Gly Ser Gly Ser Gly Thr Asp Tyr Thr Leu
    195                 200                 205

Thr Ile Ser Ser Val Gln Ala Glu Asp Leu Ala Leu His Tyr Cys Gln
210                 215                 220

Gln His Tyr Arg Val Pro Tyr Thr Phe Gly Gly Gly Thr Lys Leu Glu
                225                 230                 235                 240

Ile Lys Arg Ala Asp Gly Gly Gly Gly Cys
            245                 250
```

( 2 ) INFORMATION FOR SEQ ID NO: 9:

( i ) SEQUENCE CHARACTERISTICS:
    ( A ) LENGTH: 56 base pairs
    ( B ) TYPE: nucleic acid
    ( C ) STRANDEDNESS: single
    ( D ) TOPOLOGY: linear ( i i ) MOLECULE TYPE: cDNA ( i x ) FEATURE:
    ( A ) NAME/KEY: misc_feature
    ( B ) LOCATION: 1..56
    ( C ) OTHER INFORMATION: /note= "PAC1SIG"

( x i ) SEQUENCE DESCRIPTION: SEQ ID NO: 9:

```
ATGAAGTTGC CTGTTAGGCT GTTGGTGCTG ATGTTCTGGA TTCCTGCTTC CAGCAG        56
```

( 2 ) INFORMATION FOR SEQ ID NO: 10:

( i ) SEQUENCE CHARACTERISTICS:
        ( A ) LENGTH: 56 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: misc_feature
        ( B ) LOCATION: 1..56
        ( C ) OTHER INFORMATION: /note= "520C9SIG"

( x i ) SEQUENCE DESCRIPTION: SEQ ID NO: 10:

```
ATGGCTTGGG TGTGGACCTT GCTATTCCTG ATGGCAGCTG CCCAAAGTGC CCAAAC        56
```